US 8,346,356 B2

(12) United States Patent
Girouard et al.

(10) Patent No.: US 8,346,356 B2
(45) Date of Patent: Jan. 1, 2013

(54) METHOD FOR PREPARING AN IMPLANTABLE CONTROLLED GENE OR PROTEIN DELIVERY DEVICE

(75) Inventors: Steven D. Girouard, Chagrin Falls, OH (US); Jeffrey Ross, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 282 days.

(21) Appl. No.: 12/731,197

(22) Filed: Mar. 25, 2010

(65) Prior Publication Data

US 2010/0179609 A1 Jul. 15, 2010

Related U.S. Application Data

(62) Division of application No. 10/890,825, filed on Jul. 14, 2004, now Pat. No. 7,729,761.

(51) Int. Cl.
*A61N 1/30* (2006.01)
(52) U.S. Cl. .......................................................... 607/3
(58) Field of Classification Search .............. 604/20, 604/21, 93.01; 607/3, 4, 14
See application file for complete search history.

(56) References Cited

U.S. PATENT DOCUMENTS

| 4,686,987 A | 8/1987 | Salo et al. |
| 5,025,786 A | 6/1991 | Siegel |
| 5,041,107 A | 8/1991 | Heil, Jr. |
| 5,042,497 A | 8/1991 | Shapland |
| 5,087,243 A | 2/1992 | Avitall |
| 5,103,821 A | 4/1992 | King |
| 5,130,141 A | 7/1992 | Law et al. |
| 5,259,380 A | 11/1993 | Mendes et al. |
| 5,284,136 A | 2/1994 | Hauck et al. |
| 5,312,453 A | 5/1994 | Shelton et al. |
| 5,314,430 A | 5/1994 | Bardy |
| 5,347,241 A | 9/1994 | Panaretos et al. |
| 5,354,264 A | 10/1994 | Bae et al. |
| 5,387,419 A | 2/1995 | Levy et al. |
| 5,486,359 A | 1/1996 | Caplan et al. |
| 5,507,724 A | 4/1996 | Hofmann et al. |
| 5,543,318 A | 8/1996 | Smith et al. |
| 5,558,632 A | 9/1996 | Lloyd et al. |
| 5,571,151 A | 11/1996 | Gregory |
| 5,580,779 A | 12/1996 | Smith et al. |
| 5,603,331 A | 2/1997 | Heemels et al. |
| 5,610,172 A | 3/1997 | Weidmann et al. |
| 5,704,908 A | 1/1998 | Hofmann et al. |
| 5,807,306 A | 9/1998 | Shapland et al. |

(Continued)

FOREIGN PATENT DOCUMENTS

JP 2002-522103 A 7/2002

(Continued)

OTHER PUBLICATIONS

"Japanese Application Serial No. 2007-515663, Office Action mailed Nov. 14, 2011", (w/ English Translation), 5 pgs.

(Continued)

*Primary Examiner* — Brian T Gedeon
(74) *Attorney, Agent, or Firm* — Schwegman Lundberg & Woessner, P.A.

(57) ABSTRACT

An implantable system which includes a gene/protein delivery device and a pulse generator, as well as method of preparing the gene/protein delivery device and using the system, are provided. In one embodiment, the implantable system detects a predetermined condition or event and, in response, delivers gene(s) and/or protein(s) in conjunction with delivering pacing and/or defibrillation pulses.

20 Claims, 3 Drawing Sheets

U.S. PATENT DOCUMENTS

| | | |
|---|---|---|
| 5,865,787 A | 2/1999 | Shapland et al. |
| 5,944,710 A | 8/1999 | Dev et al. |
| 5,968,006 A | 10/1999 | Hofmann |
| 6,005,009 A | 12/1999 | Murad et al. |
| 6,066,094 A | 5/2000 | Ben-Haim |
| 6,083,930 A | 7/2000 | Roufa et al. |
| 6,112,116 A | 8/2000 | Fischell et al. |
| 6,117,296 A | 9/2000 | Thomson |
| 6,119,554 A | 9/2000 | Plankenhorn |
| 6,132,419 A | 10/2000 | Hofmann |
| 6,184,030 B1 | 2/2001 | Katoot et al. |
| 6,185,461 B1 | 2/2001 | Er |
| 6,245,566 B1 | 6/2001 | Gearhart et al. |
| 6,272,377 B1 | 8/2001 | Sweeney et al. |
| 6,388,043 B1 | 5/2002 | Langer et al. |
| 6,436,672 B1 | 8/2002 | Tomlinson |
| 6,459,929 B1 | 10/2002 | Hopper et al. |
| 6,468,985 B1 | 10/2002 | Huang |
| 6,490,482 B2 | 12/2002 | Mori et al. |
| 6,571,125 B2 | 5/2003 | Thompson |
| 6,596,745 B2 | 7/2003 | Gall |
| 6,610,716 B2 | 8/2003 | Wagle et al. |
| 6,628,987 B1 | 9/2003 | Hill et al. |
| 6,654,636 B1 | 11/2003 | Dev et al. |
| 6,660,737 B2 | 12/2003 | Almstead et al. |
| 6,662,044 B2 | 12/2003 | Crawford et al. |
| 6,666,826 B2 | 12/2003 | Salo et al. |
| 6,678,556 B1 | 1/2004 | Nolan et al. |
| 6,697,669 B2 | 2/2004 | Dev et al. |
| 6,733,996 B2 | 5/2004 | Froehlich et al. |
| 6,759,236 B1 | 7/2004 | Fung et al. |
| 6,775,569 B2 | 8/2004 | Mori et al. |
| 6,801,805 B2 | 10/2004 | Stokes et al. |
| 6,810,286 B2 | 10/2004 | Donovan et al. |
| 6,919,207 B2 | 7/2005 | Goodman et al. |
| 6,969,382 B2 | 11/2005 | Richter |
| 6,976,982 B2 | 12/2005 | Santini, Jr. et al. |
| 7,039,462 B2 | 5/2006 | Pastore et al. |
| 7,072,711 B2 | 7/2006 | Girouard et al. |
| 7,142,919 B2 | 11/2006 | Hine et al. |
| 7,317,950 B2 | 1/2008 | Lee |
| 7,400,931 B2 | 7/2008 | Mandrusov et al. |
| 7,621,906 B2 | 11/2009 | Pastore et al. |
| 7,764,995 B2 | 7/2010 | Girouard et al. |
| 2002/0010492 A1 | 1/2002 | Donovan et al. |
| 2002/0019350 A1 | 2/2002 | Levine et al. |
| 2002/0022022 A1 | 2/2002 | Shi et al. |
| 2002/0031827 A1 | 3/2002 | Kanno et al. |
| 2002/0035346 A1 | 3/2002 | Reynolds et al. |
| 2002/0049154 A1 | 4/2002 | Grissom et al. |
| 2002/0055705 A1 | 5/2002 | Talpade et al. |
| 2002/0065243 A1 | 5/2002 | Fung et al. |
| 2002/0072785 A1 | 6/2002 | Nelson et al. |
| 2002/0099026 A1 | 7/2002 | Goodman et al. |
| 2002/0107553 A1 | 8/2002 | Hill et al. |
| 2002/0110910 A1 | 8/2002 | Gwathmey et al. |
| 2002/0124855 A1 | 9/2002 | Chachques |
| 2002/0147329 A1 | 10/2002 | Luyten et al. |
| 2002/0155101 A1 | 10/2002 | Donahue et al. |
| 2002/0161410 A1 | 10/2002 | Kramer et al. |
| 2002/0172663 A1 | 11/2002 | Palasis et al. |
| 2002/0183682 A1 | 12/2002 | Darvish et al. |
| 2002/0183686 A1 | 12/2002 | Darvish et al. |
| 2003/0026784 A1 | 2/2003 | Koch et al. |
| 2003/0036773 A1 | 2/2003 | Whitehurst et al. |
| 2003/0040777 A1 | 2/2003 | Shemer et al. |
| 2003/0044802 A1 | 3/2003 | Sayler et al. |
| 2003/0045830 A1 | 3/2003 | de Bizemont et al. |
| 2003/0059463 A1 | 3/2003 | Lahtinen |
| 2003/0060854 A1 | 3/2003 | Zhu |
| 2003/0073235 A1 | 4/2003 | Lagarias et al. |
| 2003/0087264 A1 | 5/2003 | Kaplitt et al. |
| 2003/0087867 A1 | 5/2003 | Vogels et al. |
| 2003/0105493 A1 | 6/2003 | Salo |
| 2003/0138415 A1 | 7/2003 | Shepard |
| 2003/0144702 A1 | 7/2003 | Yu et al. |
| 2003/0144703 A1 | 7/2003 | Yu et al. |
| 2003/0148351 A1 | 8/2003 | Henry et al. |
| 2003/0148968 A1 | 8/2003 | Hammond et al. |
| 2003/0149420 A1 | 8/2003 | Richter |
| 2003/0153952 A1 | 8/2003 | Auricchio et al. |
| 2003/0167081 A1 | 9/2003 | Zhu et al. |
| 2003/0199813 A1 | 10/2003 | Struble |
| 2003/0204206 A1 | 10/2003 | Padua et al. |
| 2003/0216476 A1 | 11/2003 | Kleemann |
| 2004/0005295 A1 | 1/2004 | Lee et al. |
| 2004/0030379 A1 | 2/2004 | Hamm et al. |
| 2004/0038400 A1 | 2/2004 | Froehlich et al. |
| 2004/0048286 A1 | 3/2004 | Lee |
| 2004/0073260 A1 | 4/2004 | Brighton |
| 2004/0088017 A1 | 5/2004 | Sharma et al. |
| 2004/0098075 A1 | 5/2004 | Lee |
| 2004/0106954 A1 | 6/2004 | Whitehurst et al. |
| 2004/0122478 A1 | 6/2004 | Stadler et al. |
| 2004/0131601 A1 | 7/2004 | Epstein et al. |
| 2004/0132184 A1 | 7/2004 | Dennis et al. |
| 2004/0158289 A1 | 8/2004 | Girouard et al. |
| 2004/0158290 A1 | 8/2004 | Girouard et al. |
| 2004/0186546 A1 | 9/2004 | Mandrusov et al. |
| 2004/0230274 A1 | 11/2004 | Heil et al. |
| 2005/0005923 A1 | 1/2005 | Herrin |
| 2005/0008628 A1 | 1/2005 | Feld et al. |
| 2005/0021091 A1 | 1/2005 | Laske et al. |
| 2005/0043675 A1 | 2/2005 | Pastore et al. |
| 2005/0059153 A1 | 3/2005 | George et al. |
| 2005/0059999 A1 | 3/2005 | Mongeon et al. |
| 2005/0096701 A1 | 5/2005 | Donovan et al. |
| 2005/0118144 A1 | 6/2005 | Zhang |
| 2005/0123526 A1 | 6/2005 | Shafer |
| 2005/0130136 A1 | 6/2005 | Lee |
| 2005/0137626 A1 | 6/2005 | Pastore et al. |
| 2005/0137631 A1 | 6/2005 | Yu et al. |
| 2005/0192637 A1 | 9/2005 | Girouard et al. |
| 2005/0245972 A1 | 11/2005 | Onyekaba et al. |
| 2005/0283197 A1 | 12/2005 | Daum et al. |
| 2005/0288721 A1 | 12/2005 | Girouard et al. |
| 2006/0047318 A1 | 3/2006 | Pastore et al. |
| 2007/0027487 A1 | 2/2007 | Mika et al. |
| 2010/0286592 A1 | 11/2010 | Girouard et al. |

FOREIGN PATENT DOCUMENTS

| | | |
|---|---|---|
| JP | 2004-508110 A | 3/2004 |
| JP | 2004-516274 A | 6/2004 |
| JP | 2006-506207 A | 2/2006 |
| JP | 5021463 | 6/2012 |
| WO | WO-98/02040 A1 | 1/1998 |
| WO | WO-98/02150 A1 | 1/1998 |
| WO | WO-98/15317 A1 | 4/1998 |
| WO | WO-99/04851 | 2/1999 |
| WO | WO-99/25385 A1 | 5/1999 |
| WO | WO-99/36563 | 7/1999 |
| WO | WO-00/07497 A1 | 2/2000 |
| WO | WO-00/62855 A1 | 10/2000 |
| WO | WO-00/74773 A1 | 12/2000 |
| WO | WO-02/20088 A1 | 3/2002 |
| WO | WO-02/49669 A2 | 6/2002 |
| WO | WO-02/49714 A2 | 6/2002 |
| WO | WO-02/087681 A2 | 11/2002 |
| WO | WO-2004/026394 A1 | 4/2004 |
| WO | WO-2004/045709 A1 | 6/2004 |
| WO | WO-2004/080533 A1 | 9/2004 |
| WO | WO-2004/093969 A1 | 11/2004 |
| WO | WO-2005/084751 A2 | 9/2005 |
| WO | WO-2006/019856 A1 | 2/2006 |

OTHER PUBLICATIONS

"Japanese Application Serial No. 2007-521625, Response filed Dec. 19, 2011 to Office Action mailed Sep. 20, 2011", (w/ English Translation of Amended Claims), 66 pgs.

"U.S. Appl. No. 10/788,906, Response filed Apr. 19, 2007 to Final Office Action mailed Oct. 2, 2006", 25 pgs.

"U.S. Appl. No. 10/788,906, Examiner Interview Summary mailed Apr. 23, 2007", 3 pgs.

"U.S. Appl. No. 10/788,906, Examiner Interview Summary mailed Jun. 11, 2008", 2 pgs.

"U.S. Appl. No. 10/788,906, Final Office Action mailed Mar. 18, 2010", 9 pgs.
"U.S. Appl. No. 10/788,906, Final Office Action mailed Dec. 10, 2008", 15 pgs.
"U.S. Appl. No. 10/788,906, Non-Final Office Action mailed Jun. 11, 2008", 14 pgs.
"U.S. Appl. No. 10/788,906, Non-Final Office Action mailed Jun. 22, 2009", 9 pgs.
"U.S. Appl. No. 10/788,906, Response filed Feb. 20, 2008 to Final Office Action mailed Dec. 4, 2007", 26 pgs.
"U.S. Appl. No. 10/788,906, Response filed Apr. 9, 2009 to Final Office Action mailed Dec. 10, 2008", 24 pgs.
"U.S. Appl. No. 10/788,906, Response filed Sep. 11, 2008 to Non Final Office Action mailed Jun. 11, 2008", 24 pgs.
"U.S. Appl. No. 10/788,906, Response filed Oct. 22, 2009 to Non Final Office Action mailed Jun. 22, 2009", 24 pgs.
"U.S. Appl. No. 10/788,906, Response filed Oct. 24, 2005 to Restriction Requirement mailed Sep. 23, 2005", 23 pgs.
"U.S. Appl. No. 10/788,906, Restriction Requirement mailed Sep. 23, 2005", 12 pgs.
"U.S. Appl. No. 10/788,906, Supplemental Amendment and Response filed Apr. 24, 2007 to Final Office Action mailed Oct. 2, 2006", 25 pgs.
"U.S. Appl. No. 10/862,716, Final Office Action mailed Jul. 13, 2007", 16 pgs.
"U.S. Appl. No. 10/862,716, Final Office Action mailed Aug. 20, 2008", 6 pgs.
"U.S. Appl. No. 10/862,716, Non Final Office Action mailed Sep. 19, 2007", 28 pgs.
"U.S. Appl. No. 10/862,716, Non Final Office Action mailed Dec. 14, 2006", 10 pgs.
"U.S. Appl. No. 10/862,716, Non-Final Office Action mailed May 1, 2009", 9 pgs.
"U.S. Appl. No. 10/862,716, Notice of Allowance mailed Mar. 23, 2010", 4 pgs.
"U.S. Appl. No. 10/862,716, Response filed Feb. 4, 2009 to Restriction Requirement mailed Dec. 5, 2008", 23 pgs.
"U.S. Appl. No. 10/862,716, Response filed Mar. 14, 2007 to Non Final Office Action mailed Dec. 14, 2006", 18 pgs.
"U.S. Appl. No. 10/862,716, Response filed Jun. 30, 2009 to Non Final Office Action mailed May 1, 2009", 10 pgs.
"U.S. Appl. No. 10/862,716, Response filed Sep. 12, 2007 to Final Office Action mailed Jul. 13, 2007", 24 pgs.
"U.S. Appl. No. 10/862,716, Response filed Nov. 19, 2008 to Final Office Action mailed Aug. 20, 2008", 11 pgs.
"U.S. Appl. No. 10/862,716, Response filed Dec. 19, 2007 to Non-Final Office Action mailed Sep. 19, 2007", 18 pgs.
"U.S. Appl. No. 10/925,508, Advisory Action mailed Oct. 14, 2008", 3 pgs.
"U.S. Appl. No. 10/925,508, Final Office Action mailed Jul. 23, 2007", 10 pgs.
"U.S. Appl. No. 10/925,508, Final Office Action mailed Jul. 24, 2008", 7 pgs.
"U.S. Appl. No. 10/925,508, Non Final Office Action mailed Feb. 14, 2007", 11 pgs.
"U.S. Appl. No. 10/925,508, Non Final Office Action mailed mailed Jan. 17, 2008", 11 pgs.
"U.S. Appl. No. 10/925,508, Non-Final Office Action mailed Jan. 6, 2009", 8 pgs.
"U.S. Appl. No. 10/925,508, Notice of Allowance mailed Jul. 15, 2009", 7 pgs.
"U.S. Appl. No. 10/925,508, Response filed Jan. 15, 2007 to Restriction Requirement mailed Dec. 13, 2006", 13 pgs.
"U.S. Appl. No. 10/925,508, Response filed Apr. 6, 2009 to Non Final Office Action mailed Jan. 6, 2009", 8 pgs.
"U.S. Appl. No. 10/925,508, Response filed Apr. 17, 2008 to Non-Final Office Action mailed Jan. 17, 2008", 13 pgs.
"U.S. Appl. No. 10/925,508, Response filed May 10, 2007 to Non Final Office Action mailed Feb. 14, 2007", 19 pgs.
"U.S. Appl. No. 10/925,508, Response filed Sep. 22, 2008 to Final Office Action mailed Jul. 24, 2008", 11 pgs.
"U.S. Appl. No. 10/925,508, Response filed Sep. 19, 2007 to Final Office Action mailed Jul. 23, 2007", 18 pgs.
"U.S. Appl. No. 10/925,508, Restriction Requirement mailed Dec. 13, 2006", 7 pgs.
"International Search Report and Written Opinion for Application No. PCT/US2005/024914, mailed Nov. 10, 2005", 17 pgs.
Avitall, B., et al., "Iontophoretic Transmyocardial Drug Delivery. A Novel Approach to Antiarrhythmic Drug Therapy", Circulation, 85(4), (1992), 1582-1593.
Baker, A. H., "Development and Use of Gene Transfer for Treatment of Cardiovascular Disease", J Card Surg, 17, (2002), 543-548.
Brugada, R., et al., "Genetics of Cardiovascular Disease with Emphasis on Atrial Fibrillation", Journal of Interventional Cardiac Electrophysiology, 3, (1999), 7-13.
Brundel, B. J. M. et al., "Alterations in Potassium Channel Gene Expression in Atria of Patients With Persistent and Paroxysmal Atrial Fibrillation: Differential Regulation of Protein and mRNA Levels for $K^+$ Channels", Journal of the American College of Cardiology, 37(3), (2001), 926-932.
Buchwald, A B, et al., "Decoy Oligodeoxynucleotide Against Activator Protein-1 Reduces Neointimal Proliferation After Coronary Angioplasty in Hypercholesterolemic Minipigs", Journal of the American College of Cardiology, 39 (4), (Feb. 20, 2002), 732-738.
Burton, D. Y., et al., "The Incorporation of an Ion Channel Gene Mutation Associated with the Long QT Syndrome (Q9E-hMiRPI) in a Plasmid Vector for Site-Specific Arrhythmia Gene Therapy: In Vitro and in Vivo Feasibility Studies", Human Gene Therapy, 14, (2003), 907-922.
Cheng, C.-F., et al., "Genetic Modifiers of Cardiac Arrhythmias", TRENDS in Molecular Medicine, 9(2), (2003), 59-66.
Cleland, J. G. F., et al., "Update of Clinical Trials from the American College of Cardiology 2003. EPHESUS, SPORTIF-III, ASCOT, COMPANION, UK-PACE and T-wave Alternans", The European Journal of Heart Failure, 5, (2003), 391-398.
Daum, D. R., "Systems and Methods for Hypotension", U.S. Appl. No. 11/141,260, filed May 31, 2005, 51 pgs.
Del Monte, F., et al., "Targeting Calcium Cycling Proteins in Heart Failure Through Gene Transfer", The Journal of Physiology, 546(1), (2002), 49-61.
Dobrev, D., et al., "Molecular Basis of Downregulation of G-Protein-Coupled Inward Rectifying $K^+$ Current ($I_{K,ACh}$) in Chronic Human Atrial Fibrillation", Circulation, 104. (2001), 2551-2557.
Donahue, J. K., et al., "Focal modification of electrical conduction in the heart by viral gene transfer.", Nat Med., 6(12), (Dec. 2000), 1395-1398.
Elisseeff, J., et al., "Controlled-release of IGF-I and TGF-β1 in a photopolymerizing Hydrogel for cartilage tissue engineering", Journal of Orthopaedic Research, vol. 19, (2001), 1098-1104.
Frey, N., et al., "Decoding calcium signals involved in cardiac growth and function", Nature Medicine 6(11), (2000), 1221-1227.
Gould, P. A., et al., "Review of the Current Management of Atrial Fibrillation", Expert Opinion on Pharmacotherapy, 4(11), (2003), 1889-1899.
Gunatillake, P. A., et al., "Biodegradable Synthetic Polymers for Tissue Engineering", European Cells and Materials 5, (2003), 1-16.
Hamawy, A. H., et al., "Cardiac Angiogenesis and Gene Therapy: A Strategy for Myocardial Revascularization", Current Opinion in Cardiology, 14, (1999), 515-522.
Hong, Y. S., et al., "Localized Immunosuppression in the Cardia Allograft Induced by a New Liposome-Mediated IL-10 Gene Therapy", J. Heart Lung Transplant, 21, (2002), 1188-1200.
Huq, F., et al., "Session 5: Cellular and Subcellular Basis of Remodeling—Modulating Signalling Pathways in Hypertrophy and Heart Failure by Gene Transfer", Journal of Cardiac Failure, 8(6)(Suppl.), (2002), S389-S400.
Jayakumar, J., et al., "Gene Therapy for Myocardial Prevention—Transfection of Donor Hearts With Heat Shock Protein 70 Gene Protects Cardiac Function Against Ischemia-Reperfusion Therapy", Circulation, 102 (Suppl. III), (2000), III-302-III-306.
Kanikkannan, N., "Iontophoresis-Based Transdermal Delivery Systems", Biodrugs 16(5), (2002), 339-347.
Koch, W. J., et al., "Gene transfer of beta-adrenergic signaling components for heart failure", Journal of Cardiac Failure, 8(6 Suppl), (2002), S526-S531.

Kozarsky, K. F., "Gene Therapy for Cardiovascular Disease", *Current Opinion in Pharmacology*, 1, (2001), 197-202.

Lee, L. Y., et al., "Exogenous control of cardiac gene therapy: evidence of regulated myocardial transgene expression after adenovirus and adeno-associated virus transfer of expression cassettes containing corticosteroid response element promoters.", *J Thorac Cardiovasc Surg.*, 118(1), (Jul. 1999), 26-4, discussion 34-35.

Lin, H., et al., "Regulating genes with electromagnetic response elements", *Journal of Cellular Biochemistry*, 81(1), (2001), 143-148.

Lin, H., et al., "Specific region of the c-myc promoter is responsive to electric and magnetic fields", *Journal of Cellular Biochemistry*, 54(3), (Mar. 1994), 281-288.

Luttun, A., et al., "The Role of Proteinases in Angiogenesis, Heart Development, Restenosis, Atherosclerosis, Myocardial Ischemia, and Stroke: Insights from Genetic Studies", *Current Atherosclerosis Reports*, 2, (2000), 407-416.

MacGowan, G. A., et al., "New molecular insights into heart failure and cardiomyopathy: potential strategies and therapies", *Ir J Med Sci.*, 171(2), (Apr.-Jun. 2002), 99-104

MacNeill, MD, B. D., et al., "Targeting Signaling Pathways in Heart Failure by Gene Transfer", *Current Atherosclerosis Reports*, 5, (2003), 178-185.

Marban, E., et al., "Gene Therapy for Cardiac Arrhythmias", *Cold Spring Harbor Symposia on Quantitative Biology, vol. LXVII—The Cardiovascular System*, Published by Cold Spring Harbor Laboratory Press, (2002), 527-531.

Mbai, M., et al., "Genetic Basis for the Origin of Cardiac Arrhythmias: Implications for Therapy", *Current Cardiology Reports*, 4, (2002), 411-417.

Miller, L. W., et al., "Limitations of Current Medical Therapies for the Treatment of Heart Failure", *Reviews in Cardiovascular Medicine*, 4(Suppl. 2), (2003), S21-S29.

Nuss, H. B., et al., "Reversal of Potassium Channel Deficiency in Cells from Failing Hearts by Adenoviral Gene Transfer: A Prototype for Gene Therapy for Disorders of Cardiac Excitability and Contractility", *Gene Therapy*, 3(10), (1996), 900-912.

Oudit, G. Y., et al., "The Molecular Physiology of the Cardiac Transient Outward Potassium Current (*Ito*) in Normal and Diseased Myocardium", *J Mol Cell Cardiol 33*, (2001), 851-872.

Pastore, J. M., "Method and Apparatus for Modulating Cellular Metabolism During Post-Ischemia or Heart Failure", *U.S. Appl. No. 10/645,823, filed Aug. 21, 2003*, 46 pgs.

Patberg, K. W., et al., "Cardiac memory is associated with decreased levels of the transcriptional factor CREB modulated by angiotensin II and calcium.", *Circulation Research*, 93(5), (Sep. 5, 2003), 472-478.

Recer, P., "Researchers find first heart attack gene", *AP Science News, Science*: www.science.org, (2003), 1 pg.

Roberts, R., et al., "Genetic Aspects of Arrhythmias", *American Journal of Medical Genetics (Semin. Med. Genet.)*, 97, (2000), 310-318.

Ross, J., et al., "Use of Extracellular Matrix and Electrical Therapy", *U.S. Appl. No. 11/017,237, filed Dec. 20 2004*, 89 pgs.

Rubenstrunk, A., et al., "Transcriptional activation of the metallothionein I gene by electric pulses in vivo: basis for the development of a new gene switch system.", *The Journal of Gene Medicine*, 5(9), (Sep. 2003), 773-783.

Rutanen, J., et al., "Progress and Prospects—Post-Intervention Vessel Remodeling", *Gene Therapy*, 9, (2002), 1487-1491.

Schram, G., et al., "Differential Distribution of Cardiac Ion Channel Expression as a Basis for Regional Specialization in Electrical Function", *Circulation Research*, 90, (2002), 939-950.

Sih, Harris J., "Implantable Medical Devices Comprising Isolated Extracellular Matrix", *U.S. Appl. No. 11/017,432, filed Dec. 20, 2004*, 87 pgs.

Thijssen, V. J. L., et al., "Analysis of Altered Gene Expression During Sustained Atrial Fibrillation", *Cardiovascular Research*, 54, (2002), 427-437.

Tomaselli, F., et al., "Photodynamic Therapy Enhanced by Hyperbaric Oxygen in Acute Endoluminal Palliation of Malignant Bronchial Stenosis (Clinical Piolet Study in 40 Patients)", *European Journal of Cardio-thoracic Surgery*, 19, (2001), 549-554.

Towbin, J. A., et al., "Chapter 3—Genetics and Cardiac Arrhythmias", *In Advances in Pediatrics*, vol. 29, Published by Mosby, Inc., (2002), 87-129.

Van Gelder, MD, I. C., et al.. "Alterations in Gene Expression of Proteins Involved in the Calcium Handling in Patients with Atrial Fibrillation", *J Cardiovasc Electrophysical*, 10, (1999), 552-560.

Walther, W., et al., "Cell Type Specific and Inducible Promoters for Vectors in Gene Therapy as an Approach for Cell Targeting", *Journal of Molecular Medicine*, 74, (1996), 379-392.

Wattanapitayakul, S. K., et al., "Recent Developments in Gene Therapy for Cardiac Disease", *Biomedical & Pharmacotherapy*, 54, (2000), 487-504.

Wyman, T, et al., "Promoter-Activated Expression of Nerve Growth Factor for Treatment of Neurodegenerative Diseases", *Gene Therapy*, 6, (1999), 1648-1660.

Zou, Y., et al., "Heat Shock Transcription Factor 1 Protects Cardiomyocytes From Ischemia/Reperfusion Injury", *Circulation*, 108 (24), (2003), 3024-3030.

"U.S. Appl. No. 12/843,524, Response filed Aug. 23, 2011 to Non Final Office Action mailed Jun. 10, 2011", 10 pgs.

"U.S. Appl. No. 12/843,524, Final Office Action mailed Oct. 26, 2011", 13 pgs.

"Japanese Application Serial No. 2007-515663, Response filed Aug. 17, 2011 to Office Action dated May 24, 2011", (w/ English Translation of Amended Claims), 13 pgs.

"Japanese Application Serial No. 2007-521625, Office Action mailed Sep. 20, 2011", w/ English Translation, 4 pgs.

"U.S. Appl. No. 12/843,524, Non Final Office Action mailed Jun. 10, 2011", 14 pgs.

"European Application Serial No. 05770294.6, Communication mailed Apr. 24, 2007", 2 pgs.

"European Application Serial No. 05770294.6, Office Action mailed Nov. 11, 2010", 4 pgs.

"European Application Serial No. 05770294.6, Response filed Mar. 17, 2011 to Office Action mailed Nov. 11, 2010", 32 pgs.

"European Application Serial No. 05770294.6, Response filed May 23, 2007 to Communication mailed Apr. 24, 2007", 17 pgs.

"Japanese Application Serial No. 2007-521625, Office Action mailed Dec. 20, 2010", (w/ English Translation), 7 pgs.

"Japanese Application Serial No. 2007-521625, Response filed Mar. 23, 2011 to Office Action mailed Dec. 20, 2010", (w/ English Translation of Amended Claims), 23 pgs.

"Japanese Application Serial No. 2007-515663, Office Action mailed May 24, 2011", (w/ English Translation), 5 pgs.

"U.S. Appl. No. 12/843,524, Response filed Jan. 26, 2012 to Final Office Action mailed Oct. 26, 2011", 10 pgs.

"Japanese Application Serial No. 2007-515663, Response filed Feb. 7, 2012 to Office Action mailed Nov. 14, 2011", (w/ English Translation of Amended Claims), 14 pgs.

Cohn, JN, et al., "Cardiac remodeling—concepts and clinical implications: a consensus paper from an international forum on cardiac remodeling. Behalf of an International Forum on Cardiac Remodeling.", J Am Coll Cardiol. Mar 1, 2000;36(3)., Abstract.

US 8,346,356 B2

METHOD FOR PREPARING AN IMPLANTABLE CONTROLLED GENE OR PROTEIN DELIVERY DEVICE

CROSS REFERENCE TO RELATED APPLICATION

This application is a divisional of U.S. application Ser. No. 10/890,825, filed Jul. 14, 2004, now issued as U.S. Pat. No. 7,729,761, which is hereby incorporated by reference in its entirety.

This application is related to co-pending, commonly assigned U.S. patent application Ser. No. 10/862,716, entitled "METHOD AND APPARATUS TO MODULATE CELLULAR REGENERATION POST MYOCARDIAL INFARCT," filed on Jun. 7, 2004, now issued as U.S. Pat. No. 7,764,995, and U.S. patent application Ser. No. 10/788,906, entitled "METHOD AND APPARATUS FOR DEVICE CONTROLLED GENE EXPRESSION," filed on Feb. 27, 2004, now issued as U.S. Pat. No. 7,840,263, which are hereby incorporated by reference in their entirety.

FIELD OF THE INVENTION

This invention relates generally to gene therapy of living tissue and particularly, but not by way of limitation, to method and apparatus for delivering gene or protein using an implantable medical device.

BACKGROUND OF THE INVENTION

Many techniques currently exist for delivering drugs or other medicaments to body tissue. These include topical or transcutaneous administration where the drug is passively absorbed, or caused to pass, into or across the skin or other surface tissue; oral administration; injection directly into body tissue such as through an intramuscular injection or the like; and intravenous administration, which involves introducing a selected drug directly into the blood stream. Transcutaneous drug delivery systems are usually limited to external administration of a drug through the patient's skin or other surface tissue, and thus is inefficient because some of the drug may be absorbed by healthy tissue before it reaches the diseased or damaged area, or carried beyond the diseased or damaged area. Oral administration, injection, and intravenous administration are systemic and so fail to concentrate the drug in a local area.

Transportation of a drug using a localized drug delivery system may be enhanced through means such as iontophoresis. Iontophoresis typically involves an interaction between ionized molecules of a drug and an external electric field, which results in the migration of charged molecules. The migration is accomplished by placing two electrodes across the tissue to be treated and charging the electrodes with a relatively low, direct current (DC), voltage. One of the electrodes acts as a source electrode and is typically in contact with the drug solution. The other electrode acts as a return electrode and may be filled with an electrolyte solution. The electric field generated between the two electrodes causes the charged molecules to migrate from one electrode into the tissues to be treated.

Nevertheless, problems are associated with introducing an electrical current into the body, including muscle stimulation and contraction, as well as pain or other unwanted sensations. More importantly, the problem of cardiac arrhythmia (irregular rhythm) can easily arise when electrical current passes through the heart. The current source causing that problem can originate from an external source, within the heart itself, or adjacent to the heart, such as from a coronary artery.

Intensity (current density), frequency, waveform and duration of the electrical current used in iontophoresis have an effect on whether cardiac arrhythmias and other problems will occur, as well as the magnitude of those reactions. The threshold at which ventricular fibrillation occurs with various transthoracic and intracardiac electrical levels increases with higher frequency currents. The threshold of sensation also increases with higher frequencies. For instance, U.S. Pat. No. 5,087,243 discloses a method which attempts to minimize the risk of iontophoresis-induced arrhythmias. An implanted myocardial iontophoresis patch system is disclosed therein which a pulsed current is supplied to the anodal patch. Electrical activity in the patient's heart is monitored and the iontophoresis current is pulsed on and off in synchronization with ventricular depolarization to avoid the interval during which the heart is vulnerable to electrically induced arrhythmias or unnatural heart rhythms.

What is needed is an improved apparatus for local, transient delivery of gene(s) and/or protein(s), e.g., one which is employed in conjunction with electrical therapy.

SUMMARY OF THE INVENTION

The present invention is directed to the local, transient delivery of a therapeutic agent, such as a nucleic acid molecule (polynucleotide) or protein, from a polymer matrix to the myocardium, a vessel, or any other organ or area for which transluminal access is desirable of a mammal having or at risk of a particular condition. For example, the present invention can be used to locally administer via iontophoresis isolated nucleic acid or protein to the myocardium of a mammal having or at risk of a cardiovascular condition in response to detection of a parameter or a change in a parameter which is associated with the condition, e.g., the isolated nucleic acid and/or protein is administered in an amount effective to transiently alter, e.g., enhance, myocardial function. Iontophoresis technology uses an electrical potential or current across a permeable barrier to drive ionic molecules such as nucleic acid or protein, or drag nonionic molecules in an ionic solution. Iontophoresis offers continuous or pulsatile delivery as well as preprogrammed administration schedules. Factors affecting iontophoretic transport include pH, current density, ionic strength, concentration of the molecule to be transported, molecular size of the molecule to be transported, and the method of current application (continuous or pulse current). The charge on the molecule can be controlled by changing the pH of the solution, and so delivery can be adjusted for either cathodal or anodal iontophoresis. Iontophoresis can thus facilitate transport of the molecule and may enhance tissue penetration.

In one embodiment, a mammal has a condition associated with aberrant expression, for instance, aberrant temporal expression or aberrant levels of expression, of a gene product, e.g., under expression or lack of expression of wild-type (functional) gene product. To prevent, inhibit or treat the condition in the mammal, an implantable device in the mammal releases via iontophoresis nucleic acid from a polymer matrix which includes at least one gene or a portion thereof in sense orientation, e.g., an open reading frame for the gene product or a portion thereof which encodes a gene product with substantially the same activity as the full-length gene product. In one embodiment, myocardial tissues of a mammal are contacted with genes which directly or indirectly modulate conduction in the myocardium, e.g., genes for gene products which modulate gap junction proteins and/or ion channel proteins, or for transcriptional regulatory proteins which alter gap junction protein or ion channel protein levels. In another embodiment, atria of mammal having an aberrant $I_f$ are contacted with an implantable device which includes HCN nucleic acid operably linked to a promoter (an expression cassette) embedded in a polymer matrix. Upon detection of the aberrant $I_f$, the HCN gene is delivered to atrial cells in an amount which alters the $I_f$. Thus, for myocardial conditions, the isolated nucleic acid and/or protein embedded or applied to a polymer matrix is introduced to the epicardium, endocardium, or pericardium, thereby providing for localized transmyocardial delivery at a lower dosage relative to systemic delivery. In another embodiment, the nucleic acid in the polymer matrix encodes a dominant negative gene product which is useful to decrease expression or levels of an endogenous molecule, for instance, one which is formed of multiple subunits, one of which subunits corresponds to the gene product encoded by the nucleic acid in the polymer matrix.

In another embodiment, an implantable device in a mammal having a condition associated with under expression of a wild-type (functional) protein releases via iontophoresis the protein from a polymer matrix in an amount which is effective to prevent, inhibit or treat the condition.

Antisense oligonucleotides or polynucleotides can inhibit gene expression, mainly by binding to messenger RNA of the target gene, and thus have the ability to block the expression of gene products associated with a particular condition. Thus, in one embodiment, the nucleic acid in the polymer matrix includes a gene or a portion thereof, e.g., an oligonucleotide, in antisense orientation. In one embodiment, the presence of the nucleic acid in a cell of a mammal with a corresponding endogenous gene inhibits the expression of the endogenous gene. In one embodiment, the endogenous gene encodes a wild-type (functional) gene product which is overexpressed. In another embodiment, the endogenous gene encodes a mutant gene product, e.g., one with altered activity or a dominant negative.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document. The drawing are for illustrative purposes only and not to scale nor anatomically accurate.

DETAILED DESCRIPTION

Figure 1:
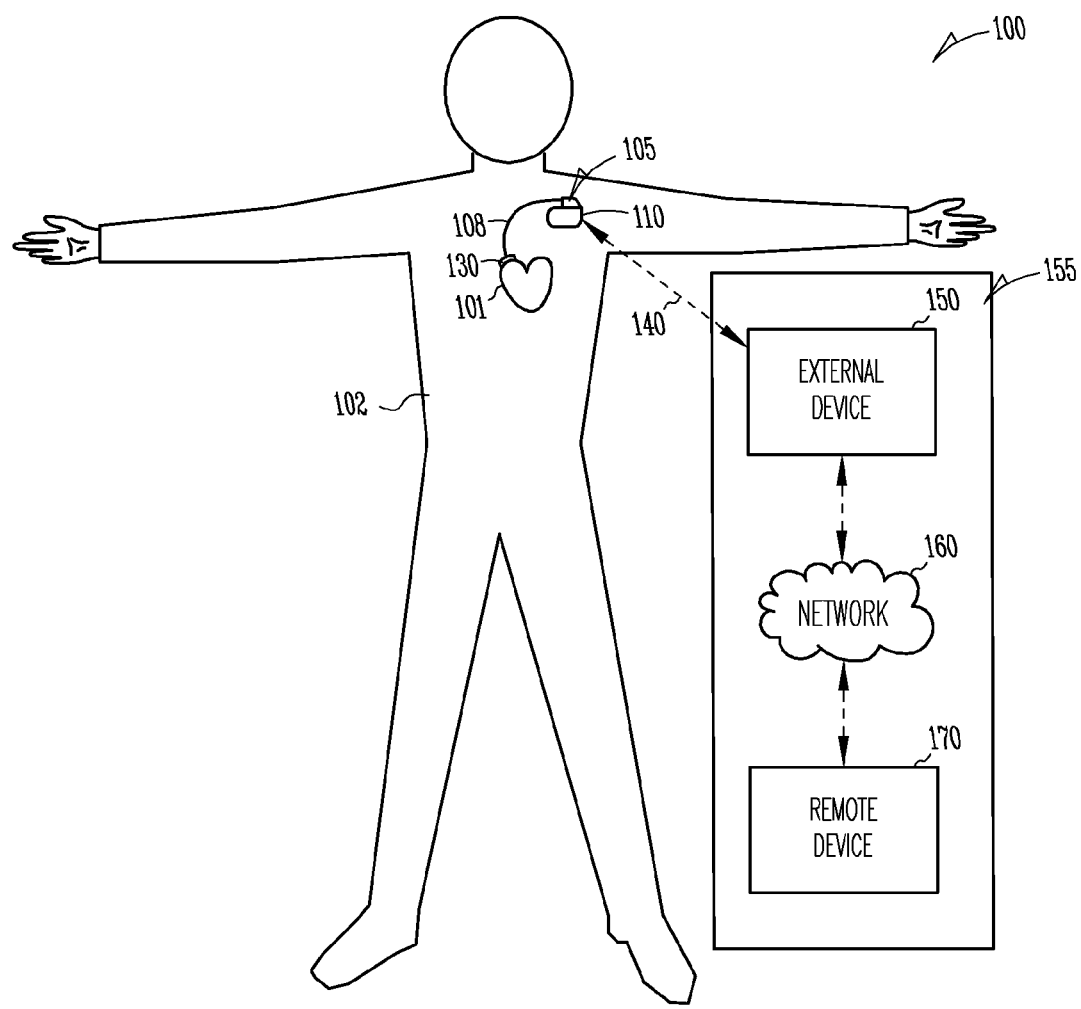
FIG. 1 is an illustration of an embodiment of a gene/protein delivery system and portions of an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

Definitions

By "nucleic acid", "oligonucleotide", and "polynucleotide" or grammatical equivalents herein means at least two nucleotides covalently linked together.

A "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA, and portions of both double stranded or single stranded sequence. The polynucleotide may be DNA, both genomic and cDNA, RNA or a hybrid, where the polynucleotide contains any combination of deoxyribo- and ribo-nucleotides, and any combination of bases, including uracil, adenine, thymine, cytosine, guanine, inosine, xathanine and hypoxathanine, etc. Thus, for example, chimeric DNA-RNA molecules may be used such as described in Cole-Strauss et al., Science, 273:1386 (1996) and Yoon et al., Proc. Natl. Acad. Sci. USA, 93:2071 (1996). It also includes modified polynucleotides such as methylated and/or capped polynucleotides.

An "oligonucleotide" includes at least 7 nucleotides, preferably 15, and more preferably 20 or more sequential nucleotides, up to 100 nucleotides, either RNA or DNA, which correspond to the complement of the non-coding strand, or of the coding strand, of a selected mRNA, or which hybridize to the mRNA or DNA encoding the mRNA and remain stably bound under moderately stringent or highly stringent conditions, as defined by methods well known to the art, e.g., in Sambrook et al., A Laboratory Manual, Cold Spring Harbor Press (1989).

The term "isolated" when used in relation to a nucleic acid, peptide or polypeptide refers to a nucleic acid sequence, peptide or polypeptide that is identified and separated from at least one contaminant nucleic acid, polypeptide or other biological component with which it is ordinarily associated in its natural source. Isolated nucleic acid, peptide or polypeptide is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and antisense strands (i.e., the molecule may be double-stranded).

"Recombinant," as applied to a polynucleotide, means that the polynucleotide is the product of various combinations of cloning, restriction and/or ligation steps, and other procedures that result in a construct that is distinct from a polynucleotide found in nature. Recombinant as applied to a protein means that the protein is the product of expression of a recombinant polynucleotide.

A "gene" generally refers to a polynucleotide or portion of a polynucleotide which includes a sequence for a gene product. For most situations, it is desirable for the gene to also comprise a promoter operably linked to the coding sequence in order to effectively promote transcription. Enhancers, repressors and other regulatory sequences may also be included in order to modulate activity of the gene, as is well known in the art.

The terms "polypeptide," "peptide," and "protein" are used interchangeably to refer to polymers of amino acids of any length. These terms also include proteins that are post-translationally modified through reactions that include glycosylation, acetylation and phosphorylation.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

"Homology" refers to the percent of identity between two polynucleotides or two polypeptides. The correspondence between one sequence and to another can be determined by techniques known in the art. For example, homology can be determined by a direct comparison of the sequence information between two polypeptide or polynucleotide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence. Thus, a "promoter," refers to a polynucleotide sequence that controls transcription of a gene or coding sequence to which it is operably linked. A large number of promoters, including constitutive, inducible and repressible promoters, from a variety of different sources, are well known in the art.

By "enhancer element" is meant a nucleic acid sequence that, when positioned proximate to a promoter, confers increased transcription activity relative to the transcription activity resulting from the promoter in the absence of the enhancer domain. Hence, an "enhancer" includes a polynucleotide sequence that enhances transcription of a gene or coding sequence to which it is operably linked. A large number of enhancers, from a variety of different sources are well known in the art. A number of polynucleotides which have promoter sequences (such as the commonly-used CMV promoter) also have enhancer sequences.

By "cardiac-specific enhancer or promoter" is meant an element, which, when operably linked to a promoter or alone, respectively, directs gene expression in a cardiac cell and does not direct gene expression in all tissues or all cell types. Cardiac-specific enhancers or promoters may be naturally occurring or non-naturally occurring. One skilled in the art will recognize that the synthesis of non-naturally occurring enhancers or promoters can be performed using standard oligonucleotide synthesis techniques.

"Operably linked" refers to a juxtaposition, wherein the components so described are in a relationship permitting them to function in their intended manner. By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. Thus, a signal or targeting peptide sequence is operably linked to another protein if the resulting fusion is secreted from a cell as a result of the presence of a secretory signal peptide or into an organelle as a result of the presence of an organelle targeting peptide.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, iontophoresis, "gene gun" delivery and various other techniques used for the introduction of polynucleotides). The introduced polynucleotide may be stably or transiently maintained in the host cell. In one embodiment, e.g., with isolated nucleic acid which is not extrachromosomally maintained or integrated into the genome of a cell, the introduced polynucleotide is transiently maintained in the cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene may include a gene which is partly or entirely heterologous (i.e., foreign) to the transgenic organism, or may represent a gene homologous to an endogenous gene of the organism.

"In vivo" gene/protein delivery, gene/protein transfer, gene/protein therapy and the like as used herein, are terms referring to the introduction of an exogenous (isolated) polynucleotide or protein directly into the body of an organism, such as a human or non-human mammal, whereby the exogenous polynucleotide or protein is introduced to a cell of such organism in vivo.

A "vector" (sometimes referred to as gene delivery or gene transfer "vehicle") refers to a macromolecule or complex of molecules comprising a polynucleotide or protein to be delivered to a host cell, either in vitro or in vivo. Vectors include, for example, expression vectors, viral vectors (such as adenoviruses ("Ad"), adeno-associated viruses (AAV), lentiviruses, poxviruses, papilloma viruses, herpesviruses, and retroviruses), liposomes and other lipid-containing complexes, and other macromolecular complexes capable of mediating or enhancing delivery of a polynucleotide or protein to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of nucleic acid or protein by the cell; components that influence localization of the polynucleotide or protein within the cell after uptake (such as agents mediating nuclear localization); and components that influence expression of polynucleotides. Such components also might include markers, such as detectable and/or selectable markers that can be used to detect or select for cells that have taken up and are expressing the introduced nucleic acid. Such components can be provided as a natural feature of the vector (such as the use of certain viral vectors which have components or functionalities mediating binding and uptake), or vectors can be modified to provide such functionalities. A large variety of such vectors are known in the art and are generally available.

A "therapeutic polynucleotide", "therapeutic gene" or "therapeutic protein" refers to a nucleotide sequence or amino acid sequence that is capable, when transferred to cells of an individual, of eliciting a prophylactic, curative or other beneficial effect in the individual.

The term "corresponds to" is used herein to mean that a polynucleotide or protein sequence is homologous (i.e., may be similar or identical, not strictly evolutionarily related) to all or a portion of a reference polynucleotide or protein sequence. In contradistinction, the term "complementary to" is used herein to mean that the complementary polynucleotide sequence is able to hybridize to the other strand. As outlined below, preferably, the homology between the two sequences is at least 70%, preferably 85%, and more preferably 95%, identical.

The terms "substantially corresponds to" or "substantial identity" or "homologous" as used herein denotes a characteristic of a nucleic acid or protein sequence, wherein a nucleic acid or protein sequence has at least about 70% sequence identity as compared to a reference sequence, typically at least about 85% sequence identity, and preferably at least about 95% sequence identity, as compared to a reference sequence. The reference sequence may be a subset of a larger sequence, such as a portion of a gene or flanking sequence, or portion of protein. However, the reference sequence is at least 20 nucleotides long, typically at least about 30 nucleotides long, and preferably at least about 50 to 100 nucleotides long, or, for peptides or polypeptides, at least 7 amino acids long, typically at least 10 amino acids long, and preferably at least 20 to 30 amino acids long. "Substantially complementary" as used herein refers to a nucleotide sequence that is complementary to a sequence that substantially corresponds to a reference sequence.

"Specific hybridization" is defined herein as the formation of hybrids between a polynucleotide which may include substitutions, deletion, and/or additions as compared to a reference sequence and a selected target nucleic acid sequence, wherein the polynucleotide preferentially hybridizes to a target nucleic acid sequence such that, for example, at least one discrete band can be identified on a Northern or Southern blot of DNA prepared from cells that contain the target nucleic acid sequence. It is evident that optimal hybridization conditions will vary depending upon the sequence composition and length(s) of the polynucleotide(s) and target(s), and the experimental method selected by the practitioner. Various guidelines may be used to select appropriate hybridization conditions (see, Maniatis et al., 1989 and Berger and Kimmel, 1987).

The term "wild-type" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the term "disease allele" refers to an allele of a gene that is capable of producing a recognizable disease. A disease allele may be dominant or recessive and may produce disease directly or when present in combination with a specific genetic background or pre-existing pathological condition. A disease allele may be present in the gene pool (an inherited disease allele) or may be generated de novo in an individual by somatic mutation (an acquired disease allele).

"Vasculature" or "vascular" are terms referring to the system of vessels carrying blood (as well as lymph fluids) throughout the mammalian body.

"Blood vessel" refers to any of the vessels of the mammalian vascular system, including arteries, arterioles, capillaries, venules, veins, sinuses, and vasa vasorum.

"Artery" refers to a blood vessel through which blood passes away from the heart. Coronary arteries supply the tissues of the heart itself, while other arteries supply the remaining organs of the body. The general structure of an artery consists of a lumen surrounded by a multi-layered arterial wall.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

By "growth factor" is meant an agent that, at least, promotes cell growth or induces phenotypic changes.

The term "angiogenic" means an agent that alone or in combination with other agents induces angiogenesis, and includes, but is not limited to, fibroblast growth factor (FGF), vascular endothelial growth factor (VEGF), hepatocyte growth factor, angiogenin, transforming growth factor (TGF), tissue necrosis factor (TNF, e.g., TNF-α), platelet derived growth factor (PDGF), granulocyte colony stimulatory factor (GCSF), placental GF, IL-8, proliferin, angiopoietin, e.g., angiopoietin-1 and angiopoietin-2, thrombospondin, ephrin-A1, E-selectin, leptin and heparin affinity regulatory peptide.

"Cardiovascular conditions" include, but are not limited to, coronary artery disease/ischemia, coronary artery disease (CAD), ischemia, angina (chest pain), thrombosis, coronary thrombosis, myocardial infarction (MI), silent ischemia, stenosis/restenosis, transient ischemic attack (TIA), atherosclerosis, peripheral vascular disease, bradyarrhythmia, e.g., bradyarrhythmia, bradycardia, sick sinus rhythm (Sick Sinus Syndrome), sinus bradycardia, sinoatrial block, asystole, sinus arrest, syncope, first degree atrio-ventricular (AV) block, second degree atrio-ventricular (AV) block, third degree atrio-ventricular (AV) block, chronotropic incompetence, tachyarrhythmia, e.g., tachyarrhythmia, tachycardia, fibrillation, flutter, atrial fibrillation, atrial flutter, familial atrial fibrillation, paroxysmal atrial fibrillation, permanent atrial fibrillation, persistent atrial fibrillation, supraventricular tachyarrhythmias, sinus tachycardia, reentry (reentrant arrhythmias), AV nodal reentry, focal arrhythmia, ectopy, ventricular fibrillation (VF), ventricular tachycardia (VT), Wolff-Parkinson-White Syndrome (WPW) and sudden cardiac death, heart failure, e.g., heart failure, cardiomyopathy, congestive heart failure, hypertrophic cardiomyopathy, remodeling, non-ischemic cardiomyopathy, dilated cardiomyopathy, restrictive cardiomyopathy, diastolic heart failure, systolic heart failure, and chronic heart failure, heart block/electrical disorders, e.g., atrioventricular (AV) block, bundle branch block (BBB), left bundle branch block (LBBB), right bundle branch block (RBBB), Long QT Syndrome (LQTS), premature ventricular contraction (PVC), electrical remodeling, intraventricular conduction defect, and hemiblock, hemodynamic deficiency, e.g., hypertension, hypotension, left ventricular dysfunction, low ejection fraction, low cardiac output, and low stroke volume, sudden cardiac death, cardiac arrest, sudden cardiac death (SCD), ventricular fibrillation, and pump failure, as well as bacterial endocarditis, viral myocarditis, pericarditis, rheumatic heart disease, and syncope. In particular, a cardiovascular condition includes, but is not limited to, arrhythmia, e.g., atrial fibrillation, ventricular fibrillation or bradycardia, ischemia, heart failure and hyperplasia not associated with neoplastic disease, which condition may be associated with ventricular remodeling, diastolic dysfunction, aberrant body temperature, aberrant or altered pressure, e.g., altered venous, left ventricular or left atrial pressure, aberrant or altered heart rate or sounds, aberrant or altered electrogram, aberrant or altered cardiac metabolism, such as altered blood pH, glucose, $pO_2$, $pCO_2$, minute ventilation, creatine, CRP, Mef2A, creatine kinase or creatine kinase MB levels, aberrant or altered pulmonary or thoracic impedance, aberrant or altered stroke volume, aberrant or altered neurohormone levels, aberrant or altered electrical activity, aberrant or altered sympathetic nerve activity, aberrant or altered renal output, aberrant or altered filtration rate, aberrant or altered angiotensin II levels, or aberrant or altered respiratory sounds, and the like.

"Treatment" or "therapy" as used herein refers to administering, to an individual patient, agents that are capable of eliciting a prophylactic, curative or other beneficial effect in the individual.

"Gene therapy" as used herein refers to administering, to an individual patient, vectors comprising a therapeutic gene.

A "user" includes a physician or other caregiver using the gene/protein delivery system to treat a patient.

General Overview

The present invention provides a system to transiently deliver one or more gene- and/or one or more protein-based therapeutic agents, as well as nongene-, nonprotein-based therapeutic agents, in a spatially controlled manner to cells or tissue of a mammal. The isolated nucleic acid, when introduced and optionally expressed in a cell, or the isolated protein when introduced to a cell, yields a cell with a different phenotype than a corresponding cell which is not contacted with the isolated nucleic acid or isolated protein. In some embodiments, the isolated nucleic acid or protein will be other than a naturally occurring sequence. In one embodiment, the mammal to be treated has or is at risk of having a cardiovascular condition. For example, the mammal may have or be at risk of having atrial fibrillation, ventricular tachycardia, heart failure, ischemia, bradycardia or hyperplasia.

This document also discusses a gene/protein delivery system that includes an implantable iontophoresis gene/protein delivery device and an implantable pulse generator. In this document, "gene/protein delivery" includes delivery of genes, proteins, and optionally other moieties useful to inhibit, prevent or treat at least one symptom (manifestation) of a condition, e.g., a cardiovascular condition. The implantable iontophoresis gene/protein delivery device is capable of delivering one or more genes and/or one or more proteins and optionally one or more non-nucleic acid, non-protein based agents to a mammal. As used herein, a "gene" includes a polynucleotide which may include a full-length open reading frame which encodes a gene product (sense orientation) or a portion thereof (sense orientation) which encodes a gene product with substantially the same activity as the gene product encoded by the full-length open reading frame, the complement of the polynucleotide, e.g., the complement of the full-length open reading frame (antisense orientation) and optionally linked 5' and/or 3' noncoding sequence(s) or a portion thereof, e.g., an oligonucleotide, which is useful to inhibit transcription, stability or translation of a corresponding mRNA. In one embodiment, a polynucleotide of the invention includes operably linked transcriptional elements including, but not limited to, a promoter, an enhancer, an intron, a Kozak sequence, or a transcription termination sequence. In another embodiment, a polynucleotide of the invention does not include a transcriptional element. In one embodiment, a polynucleotide of the invention includes modified nucleotides, e.g., those with one or more modified sugars, bases or phosphate groups. Thus, a nucleic acid of the present invention may contain phosphodiester bonds, although in some cases nucleic acid analogs are included that may have alternate backbones, comprising, for example, phosphoramide (Beaucage et al., *Methods Mol. Biol.*, 20:33 (1993); Letsinger, *J. Org. Chem.*, 35:3800 (1970); Sprinzl et al., *Eur. J. Biochem.*, 81:579 (1977); Letsinger et al., *Nucl. Acids Res.*, 14:3487 (1986)), phosphorothioate, phosphorodithioate, O-methylphosphoroamidite linkages, including morpholino modified oligo- or poly-nucleotides (Kang et al., Biopolymers, 32:1351 (1992); Summerton et al., *Antisense Nucl. Acid. Drug Dev.*, 7:187 (1997); U.S. Pat. Nos. 5,142,047 and 5,185,444), and peptide nucleic acid backbones and linkages (Nielsen, *Orig. Life Evol. Biosph.*, 23:323 (1993)). Modifications of the ribose-phosphate backbone or bases may be done to facilitate the addition of other moieties such as chemical constituents, including 2N O-methyl and 5N modified substituents, and/or to increase the stability and half-life of such molecules in physiological environments. In particular, for antisense nucleic acid which is not expressed from a vector, base modifications (Herdewijn et al., *Antisense Nucl. Acid. Drug Dev.*, 10:297 (2000); Mangos et al., *Curr. Topics Med. Chem.*, 7, 1147 (2002)); sugar modifications (Urban et al., *Farmaco*, 58:243 (2003)), e.g., arabinose derivatives (Wilds et al., *Bioconj. Chem.*, 10:299 (1999)); and phosphate modifications such as 2'-methoxyethoxy (Kimber et al., *Reprod. Biomed. Online*, 6:318 (2003)); and/or the use of 5-(N-aminohexyl)carbamoyl-2'-O-methyluridine (Ito et al., *NAR*, 31:2514 (2003)), may be employed to enhance stability in vivo. Moreover, the nucleic acid may be a chimera, e.g., made up of DNA and RNA, e.g., deoxyribonucleotides and ribonucleotides, e.g., 2'-O-methyl-ribonucleotides (see published U.S. patent application 20030045830.

The isolated nucleic acid or protein may be prepared via recombinant means or chemical synthesis. For example, the isolated nucleic acid may be a plasmid, viral vector, cosmid, phage, BAC, YAC or other artificial chromosome, isolated nucleic acid from a cell transfected with a plasmid or other vector or infected with a recombinant virus, or in vitro transcribed nucleic acid. As described above, in one embodiment, the isolated nucleic acid includes modified nucleotides, e.g., those which are more stable to hydrolysis, which nucleic acid is prepared via chemical synthesis. In one embodiment, the isolated nucleic acid is capable of being transcribed by RNA polymerase and hybridizing to target nucleic acid while in other embodiments, the isolated nucleic acid is capable of hybridizing to target nucleic acid, e.g., antisense nucleic acid, but not of being transcribed in vivo.

A protein useful in the system and methods of the invention can be synthesized in vitro, e.g., by the solid phase peptide synthetic method or by recombinant DNA approaches. The solid phase peptide synthetic method is an established and widely used method, which is described in the following references: Stewart et al., *Solid Phase Peptide Synthesis*, W.H. Freeman Co., San Francisco (1969); Merrifield, *J. Am. Chem. Soc.*, 85 2149 (1963); Meienhofer in "Hormonal Proteins and Peptides," ed.; C. H. Li, Vol. 2 (Academic Press, 1973), pp. 48-267; Bavaay and Merrifield, "The Peptides," eds. E. Gross and F. Meienhofer, Vol. 2 (Academic Press, 1980) pp. 3-285; and Clark-Lewis et al., *Meth. Enzymol.*, 287, 233 (1997). These proteins can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, of a given protein can be readily prepared. For example, amides of proteins may also be prepared by techniques well known in the art for converting a carboxylic acid group or precursor, to an amide. A preferred method for amide formation at the C-terminal carboxyl group is to cleave the protein from a solid support with an appropriate amine, or to cleave in the presence of an alcohol, yielding an ester, followed by aminolysis with the desired amine.

Salts of carboxyl groups of a protein may be prepared in the usual manner by contacting the protein with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of a protein may be prepared by utilizing an N-acyl protected amino acid for the final condensation, or by acylating a protected or unprotected protein. O-acyl derivatives may be prepared, for example, by acylation of a free hydroxy protein or protein resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the protein. Other amino-terminal modifications include aminooxypentane modifications (see Simmons et al., *Science,* 276, 276 (1997)).

In addition, the amino acid sequence of a protein can be modified so as to result in a variant. The modification includes the substitution of at least one amino acid residue in the protein for another amino acid residue, including substitutions which utilize the D rather than L form, as well as other well known amino acid analogs, e.g., unnatural amino acids such as α,α-disubstituted amino acids, N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citrulline, α-methyl-alanine, para-benzoyl-phenylalanine, phenylglycine, propargylglycine, sarcosine, ε-N,N,N-trimethyllysine, ε-N-acetyllysine, N-acetylserine, N-formylmethionine, 3-methylhistidine, 5-hydroxylysine, ω-N-methylarginine, and other similar amino acids and imino acids and tert-butylglycine.

One or more of the residues of the protein can be altered, so long as the resulting variant has substantially the same activity as that of the unmodified (functionally active) protein. For example, it is preferred that the variant has at least about 80% or more, at least 90%, the biological activity of the corresponding unmodified protein. Conservative amino acid substitutions are preferred. For example, aspartic-glutamic as acidic amino acids; lysine/arginine/histidine as basic amino acids; leucine/isoleucine/methionine/alanine/valine/glycine as hydrophobic amino acids; serine/threonine as hydrophilic amino acids. Conservative amino acid substitution also includes groupings based on side chains. In another example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant. Whether an amino acid change results in a functional protein can readily be determined by assaying the specific activity of the variant.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

The invention also envisions variants with non-conservative substitutions. Non-conservative substitutions entail exchanging a member of one of the classes described above for another.

Acid addition salts of a protein or of amino residues of the protein may be prepared by contacting the protein or amine with one or more equivalents of the desired inorganic or organic acid, such as, for example, hydrochloric acid. Esters of carboxyl groups of the proteins may also be prepared by any of the usual methods known in the art.

Moreover, it is also envisioned that the proteins are modified in a manner that increases their stability in vivo, e.g., their half-life or bioavailability. Methods to prepare such derivatives are well known to the art. One method to stabilize peptides is to prepare derivatives which are cyclized peptides (see EPA 471,453 (amide bonds), such as that between lysine and aspartic acid side chains; EPA 467,701 (disulfide bonds); EPA 467,699 (thioether bonds). Other modifications which may increase in vivo stability are disclosed in Jameson et al. (*Nature,* 368, 744 (1994)); U.S. Pat. Nos. 4,992,463; 5,596, 078 and 5,091,396.

The gene/protein delivery system of the invention detects a certain physiological signal, e.g., a change in a particular physiological parameter, indicative of a condition or the onset of a condition, e.g., a condition treatable by gene and/or protein therapy, and, in response to the detection, delivers an effective amount of the gene(s) and/or protein(s). Though discussed specifically as part of a cardiac rhythm management system, the gene/protein delivery system may be employed for all in vivo gene/protein therapies.

FIG. 1 is an illustration of an embodiment of a gene/protein delivery system 100 and portions of an environment in which it is used. System 100 includes implantable system 105, external system 155, and telemetry link 140 providing for communication between implantable system 105 and external system 155.

Implantable system 105 includes, among other things, implantable CRM device 110, lead system 108, and implantable iontophoresis gene/protein delivery device 130. As shown in FIG. 1, implantable CRM device 110 is implanted in body 102. In one embodiment, implantable CRM device 110 includes a gene/protein delivery controller. Gene/protein delivery device 130 is attached to heart 101. Lead system 108 includes one or more leads providing for communication between implantable CRM device 110 and gene/protein delivery device 130. In one embodiment, lead system 108 provides for wired communication between implantable CRM device 110 and gene/protein delivery device 130. In one embodiment, lead system 108 provides for communication between implantable CRM device 110 and gene/protein delivery device 130 through tissue conduction of an electric signal. In various embodiments, implantable CRM device 110 also includes a pacemaker, a cardioverter/defibrillator, a cardiac resynchronization therapy (CRT) device, a cardiac remodeling control therapy (RCT) device, a drug delivery device or a drug delivery controller, a cell therapy device, or any other implantable medical device. Lead system 108 further includes leads for sensing physiological signals and delivering pacing pulses, cardioversion/defibrillation shocks, and/or pharmaceutical or other substances.

External system 155 includes external device 150, network 160, and remote device 170. External device 150 is within the vicinity of implantable CRM device 110 and communicates with implantable CRM device 110 bi-directionally via telemetry link 140. Remote device 170 is in a remote location and communicates with external device 150 bi-directionally via network 160, thus allowing a user to monitor and treat a patient from a distant location.

System 100 allows gene/protein delivery to be triggered by any one of implantable CRM device 110, external device 150, or remote device 170. In one embodiment, implantable CRM device 110 triggers gene/protein delivery upon detecting a predetermined signal or condition. In another embodiment, external device 150 or remote device 170 triggers gene/protein delivery upon detecting a condition from a signal transmitted from implantable CRM device 110. In one specific embodiment, external system 155 includes a processor running a therapy decision algorithm to determine whether and when to trigger gene/protein delivery. In another specific embodiment, external system 155 includes a user interface to present signals acquired by implantable CRM device 155 and/or the detected abnormal condition to a user and receives commands from the user for triggering gene/protein delivery. In another specific embodiment, the user interface includes a user input incorporated into external device 150 to receive commands from the user and/or the patient treated with system 100. For example, the patient may be instructed to enter a command for a gene/protein delivery when he senses certain symptoms, and another person near the patient may do the same upon observing the symptoms.

Figure 2:
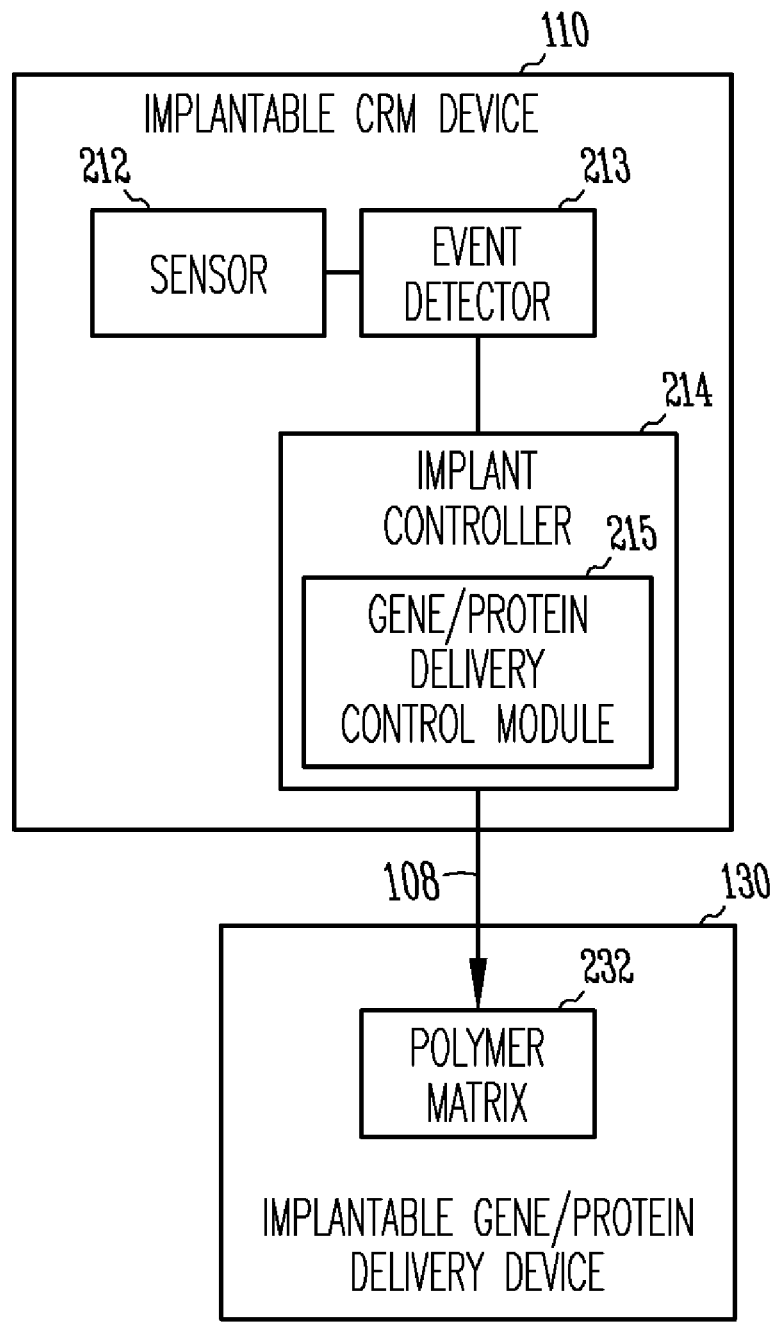
FIG. 2 is a block diagram showing one embodiment of the circuit of portions of the gene/protein delivery system such as shown in FIG. 1.

FIG. 2 is a block diagram showing one embodiment of the circuit of portions of system 100 including implantable CRM device 110, lead system 108, and gene/protein delivery device 130. In one embodiment, lead system 108 provides for an electrical connection between implantable CRM device 110 and gene/protein delivery device 130, such that the implantable CRM device transmits a voltage or current signal to the gene/protein delivery device to control gene/protein delivery. In another embodiment, lead system 108 allows an electrical field to be created at or near gene/protein delivery device 130 by an electrical signal generated from implantable CRM device 110 to control gene/protein delivery.

Gene/protein delivery device 130 includes polymer matrix 232 and isolated nucleic acid which encodes at least one gene product, isolated nucleic acid which binds at least one selected mRNA, or isolated protein, or a combination thereof. The isolated nucleic acid and/or protein are released from gene/protein delivery device 232 in response to the gene/protein delivery control signal transmitted from implantable CRM device 110. In one embodiment, gene/protein delivery device 130 includes an epicardial patch for delivering the gene(s)/protein(s) into cardiac tissue. In another embodiment, gene/protein delivery device 130 is incorporated into a vascular device such as a stent to release the gene(s) and/or protein(s) into the blood. Examples of a drug delivery device that employs iontophoresis are described in U.S. Pat. No. 5,041,107, "ELECTRICALLY CONTROLLABLE NON-OCCLUDING, BODY IMPLANTABLE DRUG DELIVERY SYSTEM" and U.S. Pat. No. 6,689,117, "DRUG DELIVERY SYSTEM FOR IMPLANTABLE MEDICAL DEVICE", both assigned to Cardiac Pacemakers, Inc., which are incorporated herein by reference in their entirety.

Implantable CRM device 110 includes sensor 212, event detector 213, and implant controller 214. Sensor 212 senses a physiological signal indicative of a condition which may be inhibited or treated with gene/protein delivery. Event detector 213 detects the condition. Implant controller 214 includes gene/protein delivery control module 215, which transmits a signal to gene/protein delivery device 130 to trigger gene/protein delivery in response to a detected condition. In one embodiment, gene/protein delivery device 130 includes polymer matrix 232 that contains one or more genes, e.g., two or more different, and/or one or more proteins, and releases the gene(s) and/or protein(s) in response to an applied electrical field. In one embodiment, an electrical field is applied to polymer matrix 232 as a voltage delivered through lead system 108. In another embodiment, such as when gene/protein delivery device 130 is not directly wired to an implantable CRM device, an electrical field is applied to polymer matrix 232 by conduction through the tissue of body 102.

In one embodiment, sensor 212 includes a cardiac sensing circuit that senses one or more electrograms, and event detector 213 detects an arrhythmia from the one or more electrograms. In one embodiment, event detector 213 detects the arrhythmia by detecting heart rate and comparing the heart rate to one or more threshold rates. A bradycardia condition is detected when the heart rate falls below a bradycardia threshold. A tachycardia condition is detected when the heart rate exceeds a tachycardia threshold. In a further embodiment, event detector 213 detects the arrhythmia by comparing morphological features of the electrogram to one or more predetermined templates. Event detector 213 includes one or more of a bradycardia detector, tachycardia detector, fibrillation detector, and any other arrhythmia detectors. In one specific embodiment, event detector 213 includes an atrial fibrillation detector. In another specific embodiment, event detector 213 includes a ventricular fibrillation detector.

In one embodiment, sensor 212 senses a physiological signal indicative of ischemia, and event detector 213 includes an ischemia detector. In one specific embodiment, sensor 212 senses an electrogram and event detector 213 runs an automatic ischemia detection algorithm to detect an ischemic condition from the electrogram. One specific example of an electrogram-based ischemia detector is discussed in Zhu et al., U.S. Pat. No. 7,340,303, "EVOKED RESPONSE SENSING FOR ISCHEMIA DETECTION," filed on Sep. 25, 2001, assigned to Cardiac Pacemakers, Inc., which is incorporated herein by reference in its entirety. In another embodiment, sensor 212 includes an electrical impedance based sensor using a low carrier frequency (e.g., 100 Hz), and event detector 213 runs an automatic ischemia detection algorithm to detect an ischemic condition from the electrical impedance signal. Tissue electrical impedance has been shown to increase significantly during ischemia, as discussed in Min et al. (*International Journal of Bioelectromagnetism,* 5:53

(2003))". Sensor 212 senses low frequency electrical impedance signal between electrodes interposed in the heart. Event detector 213 detects the ischemia as abrupt changes in impedance (such as abrupt increases in value). In another specific embodiment, sensor 212 includes a local heart motion based sensor utilizing an accelerometer located within a lead body positioned on or in the heart, and event detector 213 runs an automatic ischemia detection algorithm to detect an ischemic condition from the acceleration signal. Event detector 213 detects ischemia as an abrupt decrease in the amplitude of local cardiac accelerations.

In one embodiment, sensor 212 includes a metabolic sensor that senses a metabolic signal indicative of a cardiac metabolic level (rate of metabolism of cardiac cells). Examples of the metabolic sensor include but are not limited to a pH sensor, an oxygen pressure ($PO_2$) sensor, a carbon dioxide pressure ($PCO_2$) sensor, a glucose sensor, a creatine sensor, a C-creative protein sensor, a creatine kinase sensor, a creatine kinase-MB sensor, or any combination of such sensors. Event detector 213 determines the cardiac metabolic level from the metabolic signal and compares the cardiac metabolic level to one or more predetermined thresholds defining a normal range of cardiac metabolic level. An abnormal condition is detected when the cardiac metabolic level is outside of the normal range of cardiac metabolic level.

In one embodiment, sensor 212 includes an implantable impedance sensor to measure pulmonary impedance, or impedance of a portion of the thoracic cavity. Event detector 213 detects an abnormal condition when the impedance is out of its normal range. For example, pulmonary edema, i.e., fluid retention in the lungs resulting from the decreased cardiac output, increases pulmonary or thoracic impedance. In one specific embodiment, event detector 213 produces a signal when the pulmonary or thoracic impedance exceeds a predetermined threshold impedance. In one embodiment, the impedance sensor is a respiratory sensor that senses the patient's minute ventilation. An example of an impedance sensor sensing minute ventilation is discussed in U.S. Pat. No. 6,459,929, "IMPLANTABLE CARDIAC RHYTHM MANAGEMENT DEVICE FOR ASSESSING STATUS OF CHF PATIENTS," assigned to Cardiac Pacemakers, Inc., which is incorporated herein by reference in its entirety.

In one embodiment, sensor 212 includes a pressure sensor. Abnormal conditions including arrhythmias and heart failure cause pressures in various portions of the cardiovascular system to deviate from their normal ranges. Event detector 213 detects the abnormal condition when a pressure is outside of its normal range. In one specific embodiment, event detector 213 includes a systolic dysfunction detector to detect an abnormal condition related to pressure during the systolic phase of a cardiac cycle. In another specific embodiment, event detector 213 includes a diastolic dysfunction detector to detect an abnormal condition related to pressure during the diastolic phase of a cardiac cycle. Examples of the pressure sensor include but are not limited to a left atrial (LA) pressure sensor, a left ventricular (LV) pressure sensor, an artery pressure sensor, and a pulmonary artery pressure sensor. Pulmonary edema results in elevated LA and pulmonary arterial pressures. A deteriorated LV results in decreased LV and arterial pressures. In various embodiments, event detector 213 detects an abnormal condition when the LA pressure exceeds a predetermined threshold LA pressure level, when the pulmonary arterial pressure exceeds a predetermined threshold pulmonary arterial pressure level, when the LV pressure falls below a predetermined threshold LV pressure level, and/or when the arterial pressure falls below a predetermined threshold LV pressure level. In other embodiments, event detector 213 derives a parameter from one of these pressures, such as a rate of change of a pressure, and produces a signal when the parameter deviates from its normal range. In one embodiment, the LV pressure sensor senses the LV pressure indirectly, by sensing a signal having known or predictable relationships with the LV pressure during all or a portion of the cardiac cycle. Examples of such a signal include but are not limited to an LA pressure and a coronary vein pressure. One specific example of measuring the LV pressure using a coronary vein pressure sensor is discussed in U.S. patent application Ser. No. 10/038,936, "METHOD AND APPARATUS FOR MEASURING LEFT VENTRICULAR PRESSURE," filed on Jan. 4, 2002, assigned to Cardiac Pacemakers, Inc., which is hereby incorporated by reference in its entirety.

In one embodiment, sensor 212 includes a cardiac output or stroke volume sensor. Examples of stroke volume sensing are discussed in U.S. Pat. No. 4,686,987, "BIOMEDICAL METHOD AND APPARATUS FOR CONTROLLING THE ADMINISTRATION OF THERAPY TO A PATIENT IN RESPONSE TO CHANGES IN PHYSIOLOGIC DEMAND," and U.S. Pat. No. 5,284,136, "DUAL INDIFFERENT ELECTRODE PACEMAKER," both assigned to Cardiac Pacemakers, Inc., which are incorporated herein by reference in their entirety. Event detector 213 detects the abnormal condition when the stroke volume falls below a predetermined threshold level.

In one embodiment, sensor 212 includes a neural activity sensor to detect activities of the sympathetic nerve and/or the parasympathetic nerve. A significant decrease in cardiac output immediately stimulates sympathetic and/or the parasympathetic activities, as the autonomic nervous system attempts to compensate for deteriorated cardiac function. In one specific embodiment, a neural activity sensor includes a neurohormone sensor to sense a neurohormone level. Event detector 213 detects the abnormal condition when the hormone level exceeds a predetermined threshold level. In another specific embodiment, a neural activity sensor includes an action potential recorder to sense the electrical activities in the sympathetic nerve and/or the parasympathetic nerve. Event detector 213 detects an abnormal condition when the frequency of the electrical activities in the sympathetic and/or the parasympathetic nerves exceed a predetermined threshold level. Examples of direct and indirect neural activity sensing are discussed in U.S. Pat. No. 5,042,497, "ARRHYTHMIA PREDICTION AND PREVENTION FOR IMPLANTED DEVICES," assigned to Cardiac Pacemakers, Inc., which is hereby incorporated by reference in its entirety.

In one embodiment, sensor 212 includes a heart rate variability detector. Patients suffering acute decompensated heart failure exhibit abnormally low heart rate variability. An example of detecting the heart rate variability is discussed in U.S. Pat. No. 5,603,331, "DATA LOGGING SYSTEM FOR IMPLANTABLE CARDIAC DEVICE," assigned to Cardiac Pacemakers, Inc., which is incorporated herein by reference in their entirety. Event detector 213 detects an abnormal condition when the heart rate variability falls below a predetermined threshold level.

In one embodiment, sensor 212 includes a renal function sensor. Acute decompensated heart failure results in peripheral edema primarily because of fluid retention of the kidneys that follows the reduction in cardiac output. The fluid retention is associated with reduced renal output, decreased glomerular filtration, and formation of angiotensin. Thus, in one specific embodiment, a renal function sensor includes a renal output sensor to sense a signal indicative of the renal output. Event detector 213 detects an abnormal condition when the sensed renal output falls below a predetermined threshold. In another specific embodiment, a renal function sensor includes a filtration rate sensor to sense a signal indicative of the glomerular filtration rate. Event detector 213 detects an abnormal condition when the sensed glomerular filtration rate falls below a predetermined threshold. In yet another specific embodiment, a renal function sensor includes a chemical sensor to sense a signal indicative of angiotensin II levels. Event detector 213 detects the abnormal condition when the sensed angiotensin II levels exceed a predetermined threshold level.

In one embodiment, sensor 212 includes an acoustic sensor such as a heart sound sensor and/or a respiratory sound sensor. Arrhythmias and/or heart failure cause abnormal cardiac and pulmonary activity patterns and hence, deviation of heart sounds and respiratory sounds from their normal ranges of pattern and/or amplitude. Event detector 213 detects an abnormal condition when the heart sound or respiratory sound is out of its normal range. For example, detection of abnormal third heard sound (S3) amplitude is known to indicate heart failure. In one specific embodiment, event detector 213 detects an abnormal condition when the S3 amplitude exceeds a predetermined threshold level.

In one embodiment, sensor 212 includes a remodeling sensor to sense a signal indicative a degree of myocardial remodeling. In one specific embodiment, the remodeling sensor includes two or more piezoelectric crystals incorporated in one or more leads of lead system 108 to sense a size of an injured myocardial region such as an infarct region. The size of the injured myocardial region is estimated based on spatial information sensed by the crystals and averaged over a predetermined period of time. In one embodiment, a substantial degree of change in the size of the injured region indicates a need to start, stop, or adjust the combined electrical and agent therapies. In another specific embodiment, sensor 212 includes a hypertrophic sensor to sense a signal indicative of a degree of myocardial hypertrophy, which indicates the progress of the remodeling process. In another specific embodiment, sensor 212 includes a chemical sensor to sense the change in expression or concentration of Endothelin-1 (ET-1), BNP, or p38MAPK, which are known to change during hypertrophy response. In a further embodiment, sensor processing circuit 215 includes an event detector to detect an abnormal condition when the degree of myocardial remodeling exceeds a predetermined threshold. The degree of myocardial remodeling is represented by one or more of the degree of change in the size of the injured region, the degree of myocardial hypertrophy, and the degree of the change in expression or concentration of Endothelin-1 (ET-1), BNP, or p38MAPK.

Embodiments of sensor 212 and event detector 213 are discussed in this document by way of example, but not by way of limitation. Other methods and sensors for directly or indirectly detecting an abnormal condition treatable by the gene/protein delivery may be employed with gene/protein delivery system 100.

Implantable CRM device 110 includes a hermetically sealed metal can to house at least portion of the electronics of the device. In one embodiment, sensor 212 resides within the metal can. In another embodiment, sensor 212 is outside of the metal can. In one embodiment, sensor 212 is incorporated into a lead system 108.

Figure 3:
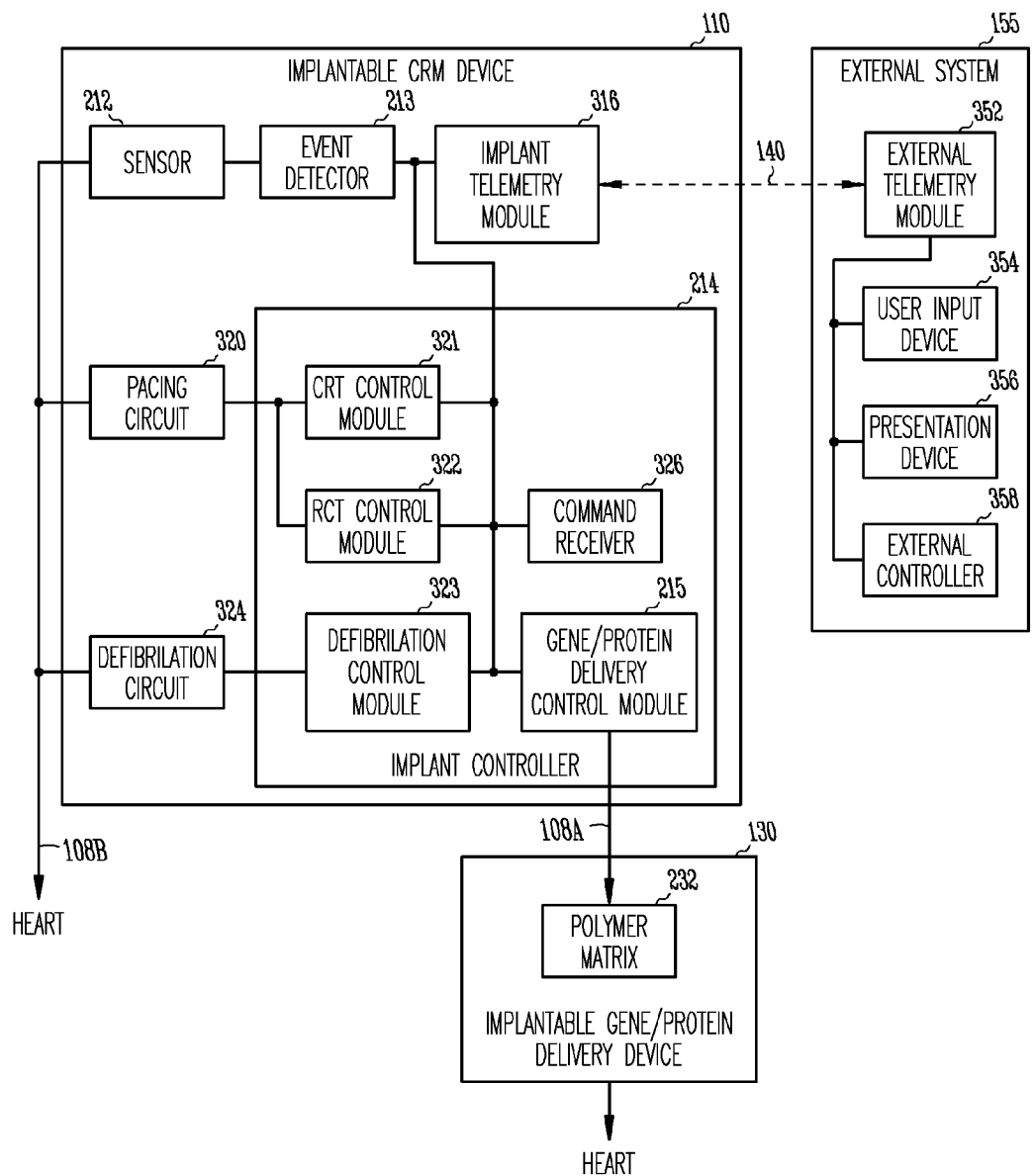
FIG. 3 is a block diagram showing a further embodiment of the circuit of portions of the gene/protein delivery system such as shown in FIG. 1.

FIG. 3 is a block diagram showing a further embodiment of the circuit of portions of system 100 including implantable CRM device 110, lead system 108, gene/protein delivery device 130, and external system 155. Implantable CRM device 110 as shown in FIG. 3 includes pacing and defibrillation capabilities. In addition to gene/protein delivery, examples of therapies delivered by implantable CRM device 110 include, but are not limited to, bradyarrhythmia pacing, anti-tachyarrhythmia pacing, atrial and/or ventricular cardioversion/defibrillation, CRT, RCT, and drug delivery. However, the pacing and defibrillation capabilities are not necessary for system 100 to perform gene/protein delivery, and hence, may be excluded from implantable CRM device 110. In other words, implantable CRM device 110 can be an implantable pacemaker and/or defibrillator with additional functions including control of gene/protein delivery, or it can be a dedicated implantable gene/protein delivery processor or controller.

In one embodiment, implantable CRM device 110 includes sensor 212, event detector 213, implant controller 214, pacing circuit 320, defibrillation circuit 324, and implant telemetry module 316. Pacing circuit 320 delivers pacing pulses to one or more cardiac regions as controlled by implant controller 214. Defibrillation circuit 324 delivers cardioversion or defibrillation shocks to one or more cardiac regions as controlled by implant controller 214. Sensor 212 senses a physiological signal indicative of a condition treatable with gene/protein delivery, and event detector 213 detects that condition, as discussed above with reference to FIG. 2. In one specific embodiment, in which implantable CRM device 110 provides for CRT and RCT pacing as well as defibrillation, implant controller 214 includes gene/protein delivery control module 215, CRT control module 321, RCT control module 322, defibrillation control module 323, and command receiver 326. Gene/protein delivery control module 215 generates a gene/protein delivery control signal in response to a condition detected by event detector 213 or a gene/protein delivery command received by command receiver 326. Command receiver 326 receives a gene/protein delivery command from external system 155 via telemetry link 140. CRT control module 321 controls the delivery of pacing pulses from pacing circuit 320 by executing a CRT algorithm. RCT control module 322 controls the delivery of pacing pulses from pacing circuit 320 by executing a RCT algorithm. Defibrillation control module 323 controls the delivery of cardioversion/defibrillation shocks from defibrillation circuit 324 when a tachyarrhythmic condition is detected. In one embodiment, defibrillation control module 323 includes an atrial defibrillation control module to control the delivery of cardioversion/defibrillation shocks to one or more of the atria. In one embodiment, defibrillation control module 323 includes a ventricular defibrillation control module to control the delivery of cardioversion/defibrillation shocks to one or more of the ventricles.

Lead system 108 includes one or more gene/protein delivery control leads, referenced as lead system 108A, and pacing leads, defibrillation leads, pacing-defibrillation leads, or any combination of such leads, referenced as lead system 108B. Lead system 108A allows gene/protein delivery control module 215 to control implantable gene/protein delivery device 130. Lead system 108B allows sensing of electrical signals from various regions of heart 101 and/or delivery of pacing pulses and/or defibrillation shocks to various regions of heart 101. The various regions of heart 101 includes regions within or about the right atrium (RA), left atrium (LA), right ventricle (RV), and left ventricle (LV). In one embodiment, lead system 108B includes one or more transvenous leads each having at least one sensing-pacing or defibrillation electrode disposed within heart 101. In one embodiment, lead system 108B includes one or more epicardial leads each having at least one sensing-pacing or defibrillation electrode disposed on heart 101. In one embodiment, lead system 108B includes at least one atrial defibrillation electrode disposed in or about one or both of the atria to allow atrial defibrillation. In one embodiment, lead system 108B includes at least one ventricular defibrillation electrode disposed in or about one or both of the ventricles to allow ventricular defibrillation. In one embodiment, sensor 212 includes at least portions of lead system 108A or 108B. In another embodiment, sensor 212 is incorporated into lead system 108A or 108B.

External system 155 includes external telemetry module 352, external user input device 354, presentation device 356, and external controller 358. These system components distribute in one or more of external device 150, network 160, or remote device 170, depending on design and medical considerations. User input device 354 receives commands and/or parameters from the user and/or the patient to control deliveries of therapy, including gene/protein delivery. Presentation device 356 displays or otherwise presents signals acquired and/or conditions detected by implantable CRM device 110. External controller 358 controls the operation of external system 155. In one embodiment, external controller 358 further provides automatic control of operations of an implantable CRM device 110. In one embodiment, user input device 352 receives the gene/protein delivery command entered by the user based on observations of the signals and/or conditions presented by presentation device 356. In another embodiment, user input device 352 receives the gene/protein delivery command entered by a patient when the patient physically senses a symptom indicative of an immediate need for the gene/protein therapy, or entered by a person near the patient who observes a symptom indicative of the immediate need for the gene/protein therapy. In a further embodiment, external controller 358 automatically analyzes the signals acquired and/or abnormal conditions detected by implantable CRM device 110, and generates a gene/protein delivery command when deemed necessary as a result of the analysis.

Telemetry link 140 is a wireless bidirectional data transmission link supported by implant telemetry module 316 and external telemetry module 352. In one embodiment, telemetry link 140 is an inductive couple formed when two coils—one connected to implant telemetry module 316 and the other connected to external telemetry module 352—are placed near each other. In another embodiment, telemetry link 140 is a far-field radio-frequency telemetry link allowing implantable CRM device 110 and external system 155 to communicate over a telemetry range that is at least ten feet.

Implantable Iontophoresis Gene/Protein Delivery Device

The system of the invention includes an implantable iontophoresis gene and/or protein delivery device coupled to an implantable pulse generator. The implantable iontophoresis gene/protein delivery device includes a polymer matrix and isolated nucleic acid which encodes at least one gene product, isolated nucleic acid which binds at least one selected mRNA, and/or isolated protein, or any combination thereof. The isolated nucleic acid or protein is selected at the discretion of the practitioner on the basis of a correlation of the sequence with a particular condition, e.g., a correlation with beneficially altering the condition. Examples of selected genes and proteins are provided below.

Exemplary Gene(s) and/or Protein(s)

For iontophoresis techniques to be used, the molecule embedded in or applied to the polymer matrix should have specific characteristics. Ideally, the molecule should have an ionic nature or have other ionic molecules bound to the molecule to promote the iontophoretic movement or transport of that molecule from the polymer matrix. Gene(s) and/or protein(s) suitable for the implantable iontophoresis gene/protein delivery device of the invention include those useful to treat, inhibit (reduce) or eliminate one or more symptoms associated with a particular condition.

In one embodiment, where an increase in a particular gene product is indicated to treat, inhibit or eliminate one or more symptoms associated with a particular condition, at least a portion of an open reading frame encoding the gene product in sense orientation is operably linked to transcriptional control elements, for instance, a heterologous transcriptional control element, optionally including a tissue-specific control element, to form an expression cassette. For example, in one embodiment, the expression cassette includes an open reading frame for connexin 43 operably linked to a cardiac-specific promoter. In another embodiment, the expression cassette includes an open reading frame for a mammalian ion channel protein which is operably linked to a viral promoter.

In another embodiment, where a decrease in a particular gene product is indicated to treat, inhibit or eliminate one or more symptoms associated with a particular condition, at least a portion of an open reading frame for that gene product in antisense orientation is operably linked to transcriptional control elements, for instance, a heterologous transcriptional control element, optionally including a tissue-specific control element, to form an expression cassette. Alternatively, antisense nucleic acid is not present in an expression cassette, i.e., not operably linked to a transcriptional control element, e.g., a promoter.

For purposes of the present invention, control elements, such as muscle-specific and inducible promoters, enhancers and the like, will be of particular use. Such control elements include, but are not limited to, those derived from the actin and myosin gene families, such as from the myoD gene family (Weintraub et al., *Science*, 251, 761 (1991)); the myocyte-specific enhancer binding factor MEF-2 (Cserjesi and Olson, *Mol. Cell. Biol.*, 11, 4854 (1991)); control elements derived from the human skeletal actin gene (Muscat et al., *Mol. Cell. Bio.*, 7, 4089 (1987)) and the cardiac actin gene; muscle creatine kinase sequence elements (Johnson et al., *Mol. Cell. Biol.*, 9, 3393 (1989)) and the murine creatine kinase enhancer (mCK) element; control elements derived from the skeletal fast-twitch troponin C gene, the slow-twitch cardiac troponin C gene and the slow-twitch troponin I gene; hypoxia-inducible nuclear factors (Semenza et al., *Proc. Natl. Acad. Sci. USA,* 88, 5680 (1991); Semenza et al., *J. Biol. Chem.,* 269, 23757); steroid-inducible elements and promoters, such as the glucocorticoid response element (GRE) (Mader and White, *Proc. Natl. Acad. Sci. USA,* 90, 5603 (1993)); the fusion consensus element for RU486 induction; and elements that provide for tetracycline regulated gene expression (Dhawan et al., *Somat. Cell. Mol. Genet.*, 21, 233 (1995); Shockett et al., *Proc. Natl. Acad. Sci. USA,* 92, 6522 (1995)).

In one embodiment, cardiac cell restricted promoters will be of particular use. Cardiac specific promoters include, but are not limited to, promoters from the following genes: a α-myosin heavy chain gene, e.g., a ventricular α-myosin heavy chain gene, β-myosin heavy chain gene, e.g., a ventricular β-myosin heavy chain gene, myosin light chain 2v gene, e.g., a ventricular myosin light chain 2 gene, myosin light chain 2a gene, e.g., a ventricular myosin light chain 2 gene, cardiomyocyte-restricted cardiac ankyrin repeat protein (CARP) gene, cardiac α-actin gene, cardiac m2 muscarinic acetylcholine gene, ANP gene, BNP gene, cardiac troponin C gene, cardiac troponin I gene, cardiac troponin T gene, cardiac sarcoplasmic reticulum Ca-ATPase gene, skeletal α-actin gene, as well as an artificial cardiac cell-specific promoter.

Further, chamber-specific promoters or enhancers may also be employed, e.g., for atrial-specific expression, the quail slow myosin chain type 3 (MyHC3) or ANP promoter, or the cGATA-6 enhancer, may be employed. For ventricle-specific expression, the iroquois homeobox gene may be employed. Examples of ventricular myocyte-specific promoters include a ventricular myosin light chain 2 promoter and a ventricular myosin heavy chain promoter.

Other sources for promoters and/or enhancers are promoters and enhancers from the Csx/NKX 2.5 gene, titin gene, α-actinin gene, myomesin gene, M protein gene, cardiac troponin T gene, RyR2 gene, Cx40 gene, and Cx43 gene, as well as genes which bind Mef2, dHAND, GATA, CarG, E-box, Csx/NKX 2.5, or TGF-beta, or a combination thereof.

Tissue-specific enhancers may also be employed. For instance, a preferred atrial-specific enhancer is the cGATA-6 enhancer. In other embodiments, the enhancer is not tissue-specific.

In yet other embodiments, the promoter is a non-muscle, non-cardiac tissue-specific promoter.

Nevertheless, other promoters and/or enhancers which are not specific for certain tissue or cells, e.g., a viral promoter such a one from an adenovirus, adeno-associated virus, retrovirus, herpesvirus or *lentivirus*, may be employed in the expression cassettes and methods of the invention. A preferred heterologous constitutive promoter is a CMV promoter which also includes an enhancer.

Preferably, the gene is also operably linked to a polyadenylation signal.

In one embodiment, the condition is a cardiovascular condition including, but not limited to, atrial fibrillation, ischemia, ventricular tachycardia, bradycardia, hyperplasia, or heart failure. Genes and corresponding proteins useful in the system and methods for cardiovascular conditions include, but are not limited to, a connexin gene, an atrial-specific ion channel protein gene, e.g., a gene product associated with $I_f$, a non-specific ion channel protein gene, e.g., a gene product associated with $I_K$, a gene product which regulates gap junctions, a gene product which alters conduction in the myocardium, a gene product which encodes a regulatory protein which blocks ion channel protein synthesis or activity, a gene product which upregulates ion channel protein synthesis or activity, a gene product which downregulates at least one ion channel protein, or a gene product which alters ion channel kinetics or voltage.

Thus, useful genes and corresponding proteins include genes for ion channels, including $K^+$, $Na^+$, $Ca^+$ and voltage activated channels, and preferably ion channels expressed in cardiac tissue, including, but not limited to, HCN (for $I_f$), Kir 2.1 (for $I_{K1}$), Kir 3.1/3.4 (for $I_{KACh}$), ERG (α subunit for $I_{Kr}$), MiRP1 (modulates $I_{Kr}$, $I_f$ and $I_{to}$), KvLQT1 (α subunit for $I_{KS}$), MinK (β subunit for $I_{KS}$), Kv4.2/4.3 (α subunit for $I_{to}$), Kv1.4 (α subunit for $I_{to}$), KChIP2 (β subunit for $I_{to}$), Kv1.5 (for $I_{Kur}$), Cav1.2 ($I_{CaL}$), Cav1.3 ($I_{Ca V}$), Cav3.1 ($I_{Ca}$), Nav1.5 ($I_{Na}$), and connexin 40, connexin 43, and connexin 45 ($I_{GJ}$) (see Schram et al., *Circ. Res.,* 90:939 (2002)), the disclosure of which is specifically incorporated by reference herein), NCX, e.g., NCX1, NCX2 and NCX3, Kir 6.1, Kir6.2, Kv1.7, Kv4.2, Kv4.3, Kv4.1 as well as Na ion channels such as SCN5A. Other genes useful in the system and methods of the invention include, but are not limited to, Galphai2 subunit, neurotensin, calmodulin, calmodulin-dependent kinase, ATF3, calcitonin gene related peptide (CGRP), NOS, e.g., nNOS, iNOS and eNOS, Nkx 2.5, dystrophin, tafazzin, cardiac actin, desmin, lamin A/C, delta sarcoglycan, cardiac β myosin heavy chain, and cardiac tropin C, β-adrenergic receptors, inhibitory guanine nucleotide protein, GPCR kinases, VEGF, placental growth factor, ACE(2), Cox2, for calcium regulation, calmodulin, CaMKII, RyR (ryanodine receptor), SERCA, calcium ATPase (CSR), phospholamban (PLB), calcineurin, and FK506 binding protein, Lbx1, AT1A receptor, AT2, p27 (KIP1), calcineurin, angiotensin IT, and HSP. To prevent, inhibit or treat heart failure, the following genes/proteins may be useful: calmodulin, CaMKII, RyR (ryanodine receptor), SERCA, calcium ATPase (CSR), phospholamban (PLB), calcineurin, and FK506 binding protein. To prevent, inhibit or treat hyperplasia, the following genes/proteins may be useful: Lbx1, AT1A receptor, AT2, p27 (KIP1), calcineurin, angiotensin II, and HSP. To prevent, inhibit or treat ischemia, the following genes/proteins may be useful: CGRP, ATF3, placental growth factor and Cox2. To increase contractility, the following genes/proteins may be useful: neurotensin and ACE(2).

Polymer Matrix

The polymer matrix may be formed of any physiologically compatible material which generally retains isolated nucleic acid and/or protein (which are charged molecules) or optionally other agents including other therapeutic agents under physiological conditions for a sustained period of time, e.g., for months or years, in the absence of an electrical field. The polymer matrix extrudes (releases) isolated nucleic acid or protein from the implantable iontophoresis gene or protein delivery device in response to an electric field created by an electrical signal. The electric signal is generated in response to the detection of a physiological signal associated with a condition, e.g., a cardiovascular condition.

The isolated nucleic acid and/or protein or optional other agent(s) may be introduced to a solution of monomers prior to polymerization or to the polymer matrix, e.g., dissolved in a solvent (e.g., water, propylene, glycol, etc.) and the resulting solution can be incorporated into the polymer matrix material. Once the isolated nucleic acid and/or protein is embedded in or applied to a polymer matrix, the resulting gene/protein delivery device can be coupled to an implantable pulse generator. Alternatively, the polymer matrix may be first coupled to the implantable pulse generator and then the isolated nucleic acid and/or protein embedded in or applied thereto, either passively or actively (through, for example, such methods as iontophoresis). Upon delivery of an electric field, the isolated nucleic acid and/or protein or optional other agent(s) is released from the matrix at a rate which is greater than the rate of release in the absence of the electric field. In particular, the isolated nucleic acid and/or protein in an implanted iontophoresis gene/protein delivery device is released to adjacent cells or tissue or the vessel lumen in response to an electric field generated by the implantable pulse generator, which release is in an amount proportional to the applied electric field. Once the electric signal is stopped, the genes and/or proteins are no longer released or released at a rate which is significantly reduced relative to the rate of release in the presence of the electric field. Thus, the delivery of the gene(s) and/or protein(s) is transient (temporary) and may be spatially controlled by the direction of the electric field and placement of the device.

The matrix materials will preferably be physiologically inert and capable of retaining the charged molecule to be delivered. Matrix materials which may be used include: polyacetic or polyglycolic acid and derivatives thereof, polyorthoesters, polyesters, polyurethanes, polyamino acids such as polylysine, lactic/glycolic acid copolymers, polyanhydrides and ion exchange resins such as sulfonated polytetrafluorethylene, or combinations thereof.

Additionally, it is possible to construct the matrices from natural proteins or materials which are crosslinked using a crosslinking agent such as 1-ethyl-3-(3-dimethylamino-propyl)carbodiimide hydrochloride. Such natural materials are those such as albumin, collagen, fibrin, gelatin, keratin, potato starch hydrolyzed for use in electrophoresis, and agaragar (agarose). Synthetic electrophoretic matrices are also suitable including polyacrylamide, acrylamide/bis-acrylamide mixtures, cellulose acetate, glyoxyl agarose, and Sephadex™ (Pharmacia Fine Chemicals, Inc.) suitable for use in isoelectrofocusing. It is also possible to use combinations of such matrices, such as the combination of polyacrylamide and agarose, in order to fabricate the cathodic matrix of the invention.

In one embodiment, the polymer matrix may include liposomes, a hydrogel, cyclodextrins, biodegradable nanocapsules or microspheres. Thus, polymer matrix includes synthetic polymers in the form of hydrogels or other porous materials, e.g., nucleic acid and/or protein permeable configurations or morphologies, such as polyvinyl alcohol, polyvinylpyrrolidone and polyacrylamide, polyethylene oxide, poly(2-hydroxyethyl methacrylate); natural polymers such as gums and starches; synthetic elastomers such as silicone rubber, polyurethane rubber; and natural rubbers, and include poly[α(4-aminobutyl)]-1-glycolic acid, polyethylene oxide (Roy et al., *Mol. Ther.*, 7:401 (2003)), poly orthoesters (Heller et al., *Adv. Drug Delivery Rev.*, 54:1015 (2002)), silk-elastin-like polymers (Megeld et al., *Pharma. Res.*, 19:954 (2002)), alginate (Wee et al., *Adv. Drug Deliv. Rev.*, 31:267 (1998)), EVAc (poly(ethylene-co-vinyl acetate), microspheres such as poly (D, L-lactide-co-glycolide) copolymer and poly (L-lactide), poly(N-isopropylacrylamide)-b-poly(D,L-lactide), a soy matrix such as one cross-linked with glyoxal and reinforced with a bioactive filler, e.g., hydroxylapatite, poly(epsilon-caprolactone)-poly(ethylene glycol) copolymers, poly (acryloyl hydroxyethyl) starch, polylysine-polyethylene glycol, an agarose hydrogel, or a lipid microtubule-hydrogel.

In one embodiment, the nucleic acid or protein is embedded in or applied to a polymer matrix, e.g., a nonionic or ionic biodegradable or nonbiodegradable matrix, including but not limited to hydrogels of poloxamers, polyacrylamide, poly(2-hydroxyethyl methacrylate), carboxyvinyl-polymers (e.g., Carbopol 934, Goodrich Chemical Co.), cellulose derivatives, e.g., methylcellulose and hydroxypropyl cellulose, polyvinyl pyrrolidone or polyvinyl alcohols.

In another embodiment, the biocompatible polymeric materials are synthetic, nonbiodegradable polymers such as polyurethanes, polydimethylsiloxanes (silicone rubbers), ethylene vinyl acetate copolymer (EVA), poly methylmethacrylate, polyamides, polycarbonates, polyesters, polyethylene, polypropylenes, polystyrenes, polyvinyl chloride, polyvinyl alcohols, polytetrafluoroethylene, or cellulose derivatives such as cellulose acetate.

In alternative embodiments, the biocompatible polymeric material is a biodegradable polymeric such as collagen, fibrin, polylactic-polyglycolic acid, or a polyanhydride. Other examples include, without limitation, any biocompatible polymer, whether hydrophilic, hydrophobic, or amphiphilic, such as ethylene vinyl acetate copolymer (EVA), polymethyl methacrylate, polyamides, polycarbonates, polyesters, polyethylene, polypropylenes, polystyrenes, polyvinyl chloride, polytetrafluoroethylene, or cellulose derivatives such as cellulose acetate. In an alternative embodiment, a biologically derived polymer, such as protein collagen, fibrin, polylactic-polyglycolic acid, or a polyanhydride, is a suitable polymeric matrix material.

The above examples are provided for reference only, and the range of suitable polymer matrix materials should not be construed as limited to those materials listed above. The polymer matrix material can be hydrophilic, hydrophobic, or amphiphilic, provided it meets the physical characteristics described above. See also U.S. Pat. No. 5,087,243 and Avitall et al., *Circ.*, 85:1582 (1992). The polymer matrix preferably stabilizes the gene(s) and/or protein(s) and other optional agents in the polymer matrix.

A polymer matrix may also be present in a selectively semipermeable membrane such as a dialysis membrane, nylon or polysulfoxy. In one embodiment, the semipermeable membrane is not biodegradable.

In another embodiment, it is possible to fabricate multiple-layered cathodic reservoirs. Such multiple-layered reservoirs will find usefulness in certain embodiments in which there is desire to have additional control over the rate at which the charged substance is electrophoresed from the matrix. Thus, where it is desired to prevent diffusion of an anionic molecule chiefly occurring at the surface of the reservoir in contact with the target tissue, a relatively strongly-cationic matrix material may be used to cap a relatively weakly-cationic matrix material. This multiple-layered matrix embodiment may be preferentially utilized where a relatively more toxic, but more efficacious molecule is to be initially utilized to lower the immediate post-implantation stimulation threshold. However, and particularly in patients with a history of cardiac arrhythmia or fibrillation, it may be useful to charge a second layer with an anti-arrhythmic or antifibrillation drug, which drug is delivered only upon the necessary physiological demand. Similar combinations may be made in patients combinations may be made in patients with histories of cardiac arrest, where thyroid hormone therapy may be desired.

When a multiple-layered matrix is used, it is also possible to sequentially deliver a gradually declining (or increasing, or cyclical) concentration of the molecule. In such an embodiment, the distal most matrix reservoir may contain a first lower dose of the molecule, followed by a next most distal matrix with a concentration of the molecule higher than the first, and so on.

Methods of Using the Implantable Systems

The implantable systems of the invention which include an implantable pulse generator and an implantable iontophoresis gene/protein delivery device may coupled to other implantable devices, e.g., a stent, shunt, indwelling catheter, lead or epicardial patch, or minimally invasive devices, e.g., a transdermal patch. Such combined devices may be introduced to vessels, e.g., a vein, or other body lumens. In one embodiment, an implantable system of the invention is introduced to a mammalian heart, e.g., to one or both atria. For example, a mammal having or at risk of having atrial fibrillation is provided with a system which includes an implantable pulse generator and an implantable iontophoresis gene/protein delivery device, which system may be coupled to the atria of the heart. Upon sensing a physiological signal indicative of atrial fibrillation, the implant controller in the implantable pulse generator produces an electric signal which results in an electric field. The isolated nucleic acid and/or protein in the implantable iontophoresis gene/protein delivery device is released to adjacent cells or tissue or the vessel lumen in response to the electric field in an amount proportional to the applied electric field. The dosage ranges for the gene(s)/protein(s) are those large enough to produce the desired effect in which the symptoms of the condition are ameliorated. The dosage should not be so large as to cause adverse side effects. Generally, nucleic acid dosages include from about 0.001 to about 500 µg, e.g., from about 0.01 µg to about 100 µg, and for protein dosages, from about 1 ng to about 10 mg, e.g., from about 1 µg to about 1 mg. Generally, the dosage will vary with the age, condition, sex and extent of the disease in the patient and can be determined by one of skill in the art. Once the electric signal is stopped, the genes and/or proteins are no longer released or released at a rate which is significantly reduced relative to the rate of release in the presence of the electric field. Thus, the delivery of the gene(s) and/or protein(s) is transient (temporary) and may be spatially controlled by the direction of the electric field and placement of the device.

In one embodiment, where the heart tissue around the entire periphery of the heart is to receive the nucleic acid/protein, it is administered to the pericardial sac. In another embodiment, nucleic acid/protein which is present in a hydrogel can be percutaneously applied to the surface of the heart applied to the heart muscle. However, it will be appreciated that the strength and/or distribution of the electric field can be controlled such that a larger or smaller area of the heart tissue can be treated.

The frequency range for iontophoresis begins at 0 Hz (dc) and increases to a maximum of about 20 MHz, with the preferred range lying between 2-15 kHz. In one embodiment, the electric field is an ac field with a dc offset. It will be understood that the frequency can be varied within these ranges to maximize the rate of iontophoretic transfer for a given drug used in the catheters of the present invention. Selecting a frequency range that is significantly higher then the intrinsic heart rate reduces the risk of inducing an arrhythmia.

The apparatus and system of the invention may be employed with other therapies, e.g., electrical therapies such as pacing, CRT, RCT and defibrillation, drug therapies, and/or non-localized gene therapy, e.g., which results in integrated genes. Other therapies may include but are not limited to treatment with growth factors and/or angiogenic factors, or drugs such as beta-adrenergic blockers, e.g., propranolol, calcium channel blockers, e.g., verapamil, angiotensin converting enzyme inhibtors, e.g., captopril, angiotension II receptor blockers, e.g., losartan, alpha adrenergic blockers, e.g., doxazosin, or hypotensive agents, e.g., reserpine, antilipemic agents, e.g., simvastatin, vasodilating agents, e.g., amyl nitrite, carvedilol, adenosine, digoxin, ibutilide, lidocaine, neseritide and the like.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed:

1. A method to prepare an implantable device for gene or protein delivery which includes the delivery of isolated nucleic acid which encodes at least one gene product or binds at least one selected mRNA in a mammal or isolated protein, comprising:
    introducing to a physiologically compatible polymer matrix the isolated nucleic acid or isolated protein, or combining physiologically compatible monomers suitable to form a polymeric matrix and the isolated nucleic acid or isolated protein, so as to yield a nucleic acid or protein containing matrix, wherein the isolated nucleic acid or protein is selected so as to prevent, inhibit or treat a cardiac condition in a mammal, and wherein the rate of release of the nucleic acid or protein from the nucleic acid or protein containing matrix is capable of being controlled by an electric signal; and
    electrically wiring the nucleic acid or protein containing matrix to an implantable device having a sensor to sense a physiological signal indicative of a predetermined cardiac condition;
    an event detector, coupled to the sensor, to detect the predetermined cardiac condition from the physiological signal; an implant telemetry module to receive an external command; and an implant controller including a gene or protein delivery control module configured to produce an electrical signal to control iontophoretic gene or protein delivery in response to the external command.

2. The method of claim 1, wherein the nucleic acid or protein is selected to prevent, inhibit or treat atrial fibrillation, heart failure, ventricular fibrillation, ischemia, brachycardia or hyperplasia.

3. The method of claim 1, wherein the nucleic acid is present on one or more vectors.

4. The method of claim 1, wherein the one or more vectors are DNA vectors.

5. The method of claim 1, wherein the one or more vectors are viral vectors.

6. The method of claim 1, wherein the one or more vectors are plasmid vectors.

7. The method of claim 1, wherein the nucleic acid includes morpholino modified nucleotides.

8. The method of claim 1, wherein at least one gene product or protein is a connexin.

9. The method of claim 1, wherein at least one gene product or protein is an atrial-specific ion channel protein.

10. The method of claim 9, wherein the gene product or protein is associated with $I_f$.

11. The method of claim 1, wherein at least one gene product or protein is a non-specific ion channel protein.

12. The method of claim 11, wherein the gene product or protein is associated with $I_{K1}$, $I_{CaL}$, $I_{to}$, $I_{Kr}$, $K_{Kur}$, $I_{KATP}$, $I_{Na}$ or $I_{Na/Ca}$.

13. The method of claim 1, wherein at least one gene product or protein regulates gap junctions.

14. The method of claim 1, wherein at least one gene product or protein alters conduction in the myocardium.

15. The method of claim 1, wherein the protein is or the nucleic acid encodes a regulatory protein that blocks ion channels, upregulates ion channels, downregulates ion channels, or alters ion channel kinetics.

16. The method of claim 1, further comprising an implantable lead system including one or more leads.

17. The method of claim 1, wherein the implantable device further comprises a pacing circuit coupled to the implant controller, and wherein the implant controller includes a pacing control module adapted to control a delivery of pacing pulses in conjunction with the release of the nucleic acid or protein.

18. The method of claim 1, wherein the implantable gene or protein delivery device comprises an epicardial patch including the polymer matrix.

19. An implantable gene or protein delivery device prepared by the method of claim 1.

20. A method to prepare an implantable device having a gene or protein delivery matrix including isolated nucleic acid which encodes at least one gene product or binds at least one selected mRNA in a mammal or isolated protein, comprising:
    providing an implantable device having a sensor to sense a physiological signal indicative of a predetermined cardiac condition; an event detector, coupled to the sensor, to detect the predetermined cardiac condition from the physiological signal; an implant telemetry module to receive an external command; and an implant controller including a gene or protein delivery control module configured to produce an electrical signal to control iontophoretic gene or protein delivery in response to the external command;

providing a matrix comprising a physiologically compatible polymer and the isolated nucleic acid or isolated protein, wherein the rate of release of the nucleic acid or protein from the matrix is capable of being controlled by the electric signal; and electrically wiring the implantable device to the matrix.

* * * * *